United States Patent [19]

Hall et al.

[11] Patent Number: 4,549,982
[45] Date of Patent: Oct. 29, 1985

[54] 1-OXOALKYL-2-ISOPROPYLNORBOR-NANE DERIVATIVES, USES THEREOF IN AUGMENTING OR ENHANCING THE AROMA OF CONSUMABLE MATERIALS AND PROCESSES FOR PREPARING SAME

[75] Inventors: John B. Hall, Rumson; Mark A. Sprecker, Sea Bright; Robert P. Belko, Woodbridge, all of N.J.; Augustinus G. Van Loveren, Rye, N.Y.; Marie R. Hanna, Hazlet, N.J.

[73] Assignee: International Flavors & Fragrances Inc., New York, N.Y.

[21] Appl. No.: 644,058

[22] Filed: Aug. 24, 1984

[51] Int. Cl.$^4$ ............ C07C 49/115; A61K 7/46
[52] U.S. Cl. ............ 252/522 R; 568/374; 568/820
[58] Field of Search ............ 568/374, 820; 252/522 R

[56] References Cited

U.S. PATENT DOCUMENTS

| | | | |
|---|---|---|---|
| 2,407,508 | 9/1946 | Morris et al. | 568/374 |
| 2,435,403 | 2/1948 | Morris et al. | 568/820 |
| 2,706,202 | 4/1955 | Bavley et al. | 568/374 |
| 3,250,815 | 5/1966 | Houlihan | 568/820 |
| 3,852,358 | 12/1974 | Hall et al. | 568/374 |

FOREIGN PATENT DOCUMENTS 59-42339  3/1984  Japan .................. 568/374

OTHER PUBLICATIONS

Tsuboi et al., Bull. Chem. Soc. of Japan, vol. 47, pp. 1673-1677 (1974).

Primary Examiner—James H. Reamer
Attorney, Agent, or Firm—Arthur L. Liberman

[57] ABSTRACT

Described are 1-oxoalkyl-2-isopropylnorbornane derivatives defined according to the generic structure:

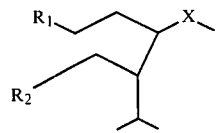

wherein X represents a moiety selected from the group consisting of:

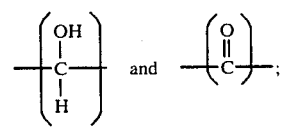

wherein the dashed line represents a carbon-carbon double bond or a carbon-carbon single bond and wherein $R_1$ and $R_2$ represent hydrogen or methyl with the proviso that $R_1$ and $R_2$ are not both methyl, and uses thereof in augmenting or enhancing the aroma of consumable materials selected from the group consisting of perfume compositions, colognes and perfumed articles. Also described are processes for preparing said 1-oxoalkyl-2-isopropylnorbornane derivatives by means of a low temperature catalytic Diels Alder reaction or high temperature thermal Diels Alder reaction between a bicyclopentadiene derivative and 2-methyl-3-buten-5-one according to the reaction:

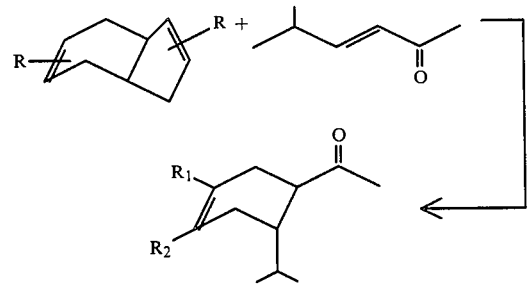

wherein R represents methyl or hydrogen.

13 Claims, 16 Drawing Figures

GLC PROFILE FOR EXAMPLE II, CRUDE.

GLC PROFILE FOR EXAMPLE I, CRUDE

FIG. 2 NMR SPECTRUM FOR EXAMPLE I.

IR SPECTRUM FOR EXAMPLE I.

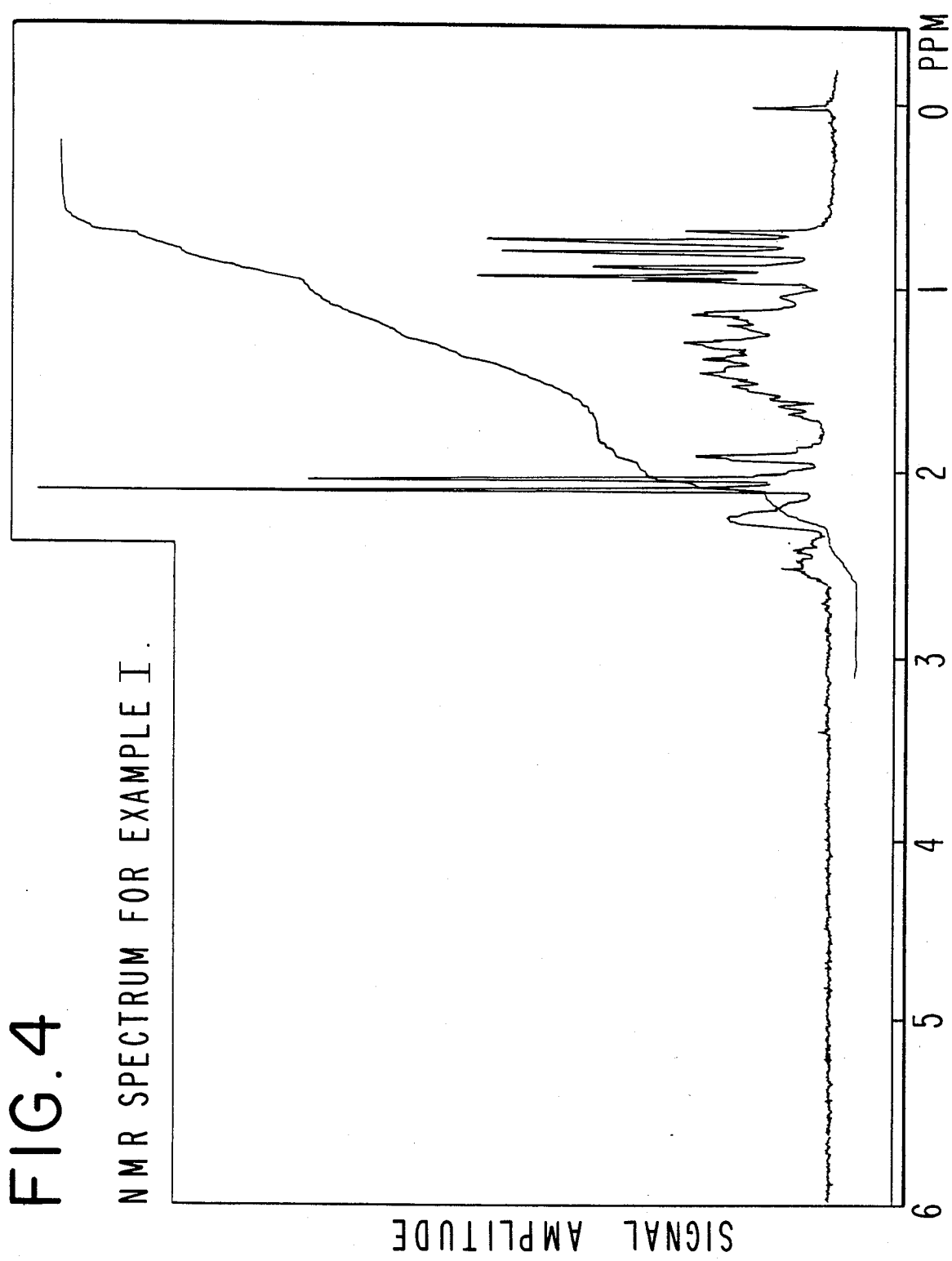

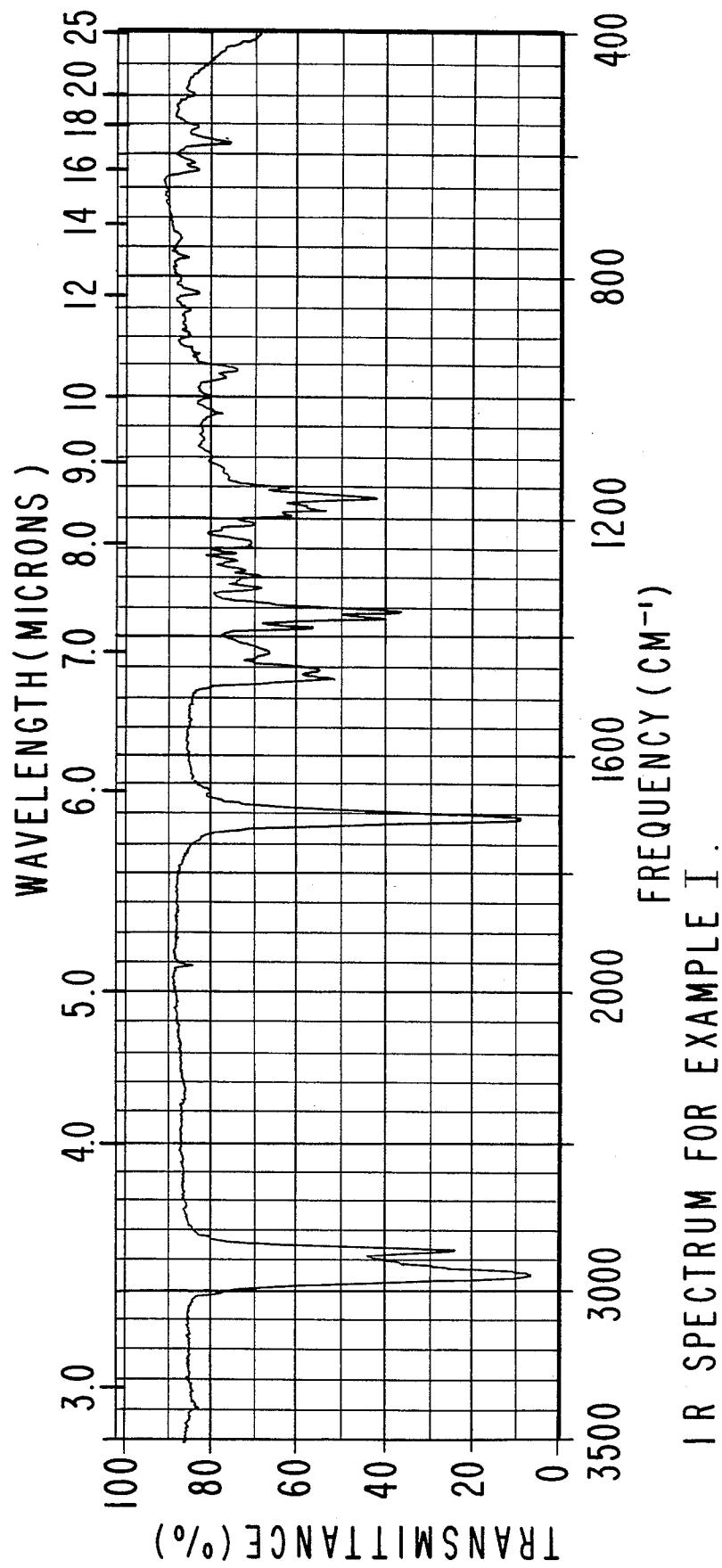

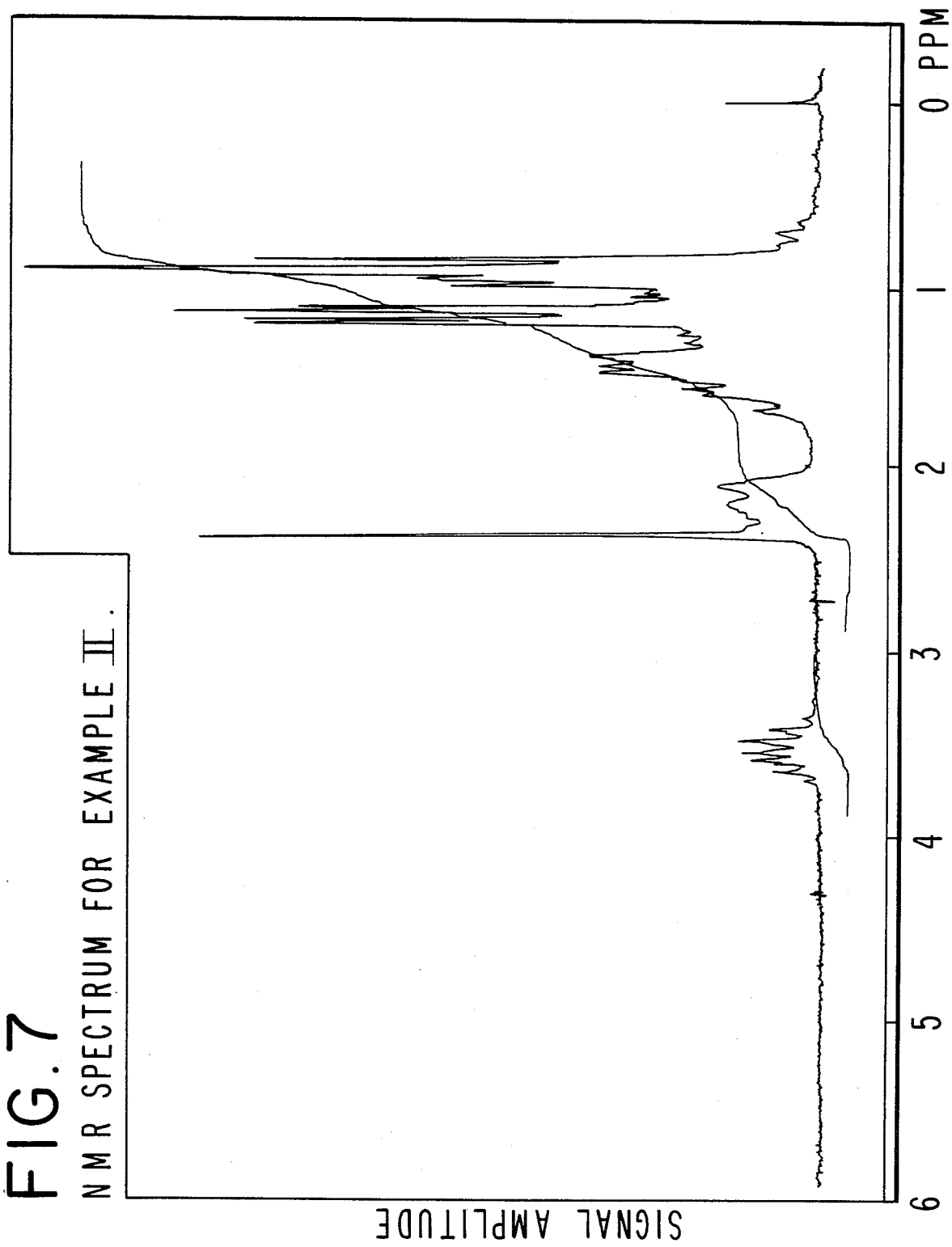
FIG. 7 NMR SPECTRUM FOR EXAMPLE II.

IR SPECTRUM FOR EXAMPLE II

GLC PROFILE FOR EXAMPLE IV.

GLC PROFILE FOR EXAMPLE III.

NMR SPECTRUM FOR EXAMPLE III.

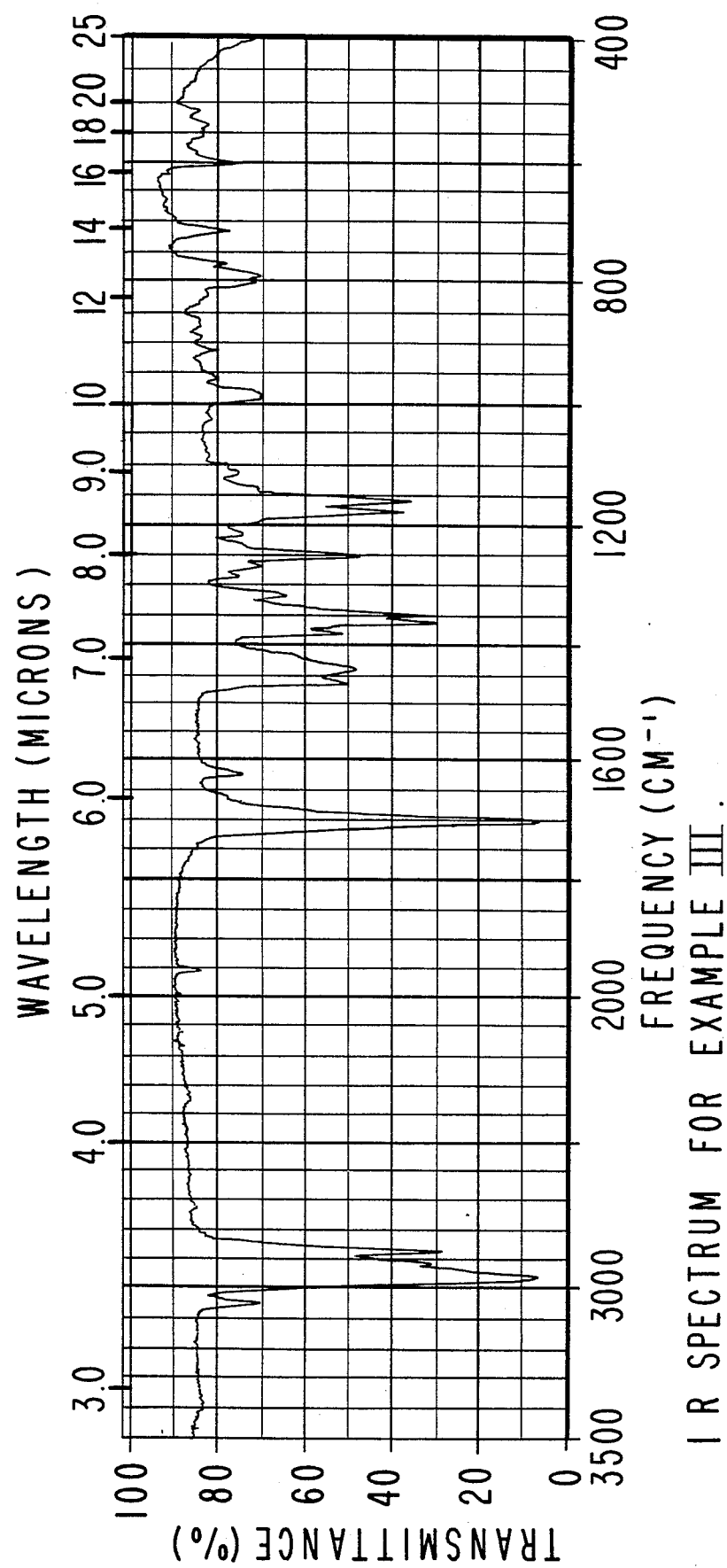
FIG. II
IR SPECTRUM FOR EXAMPLE III.

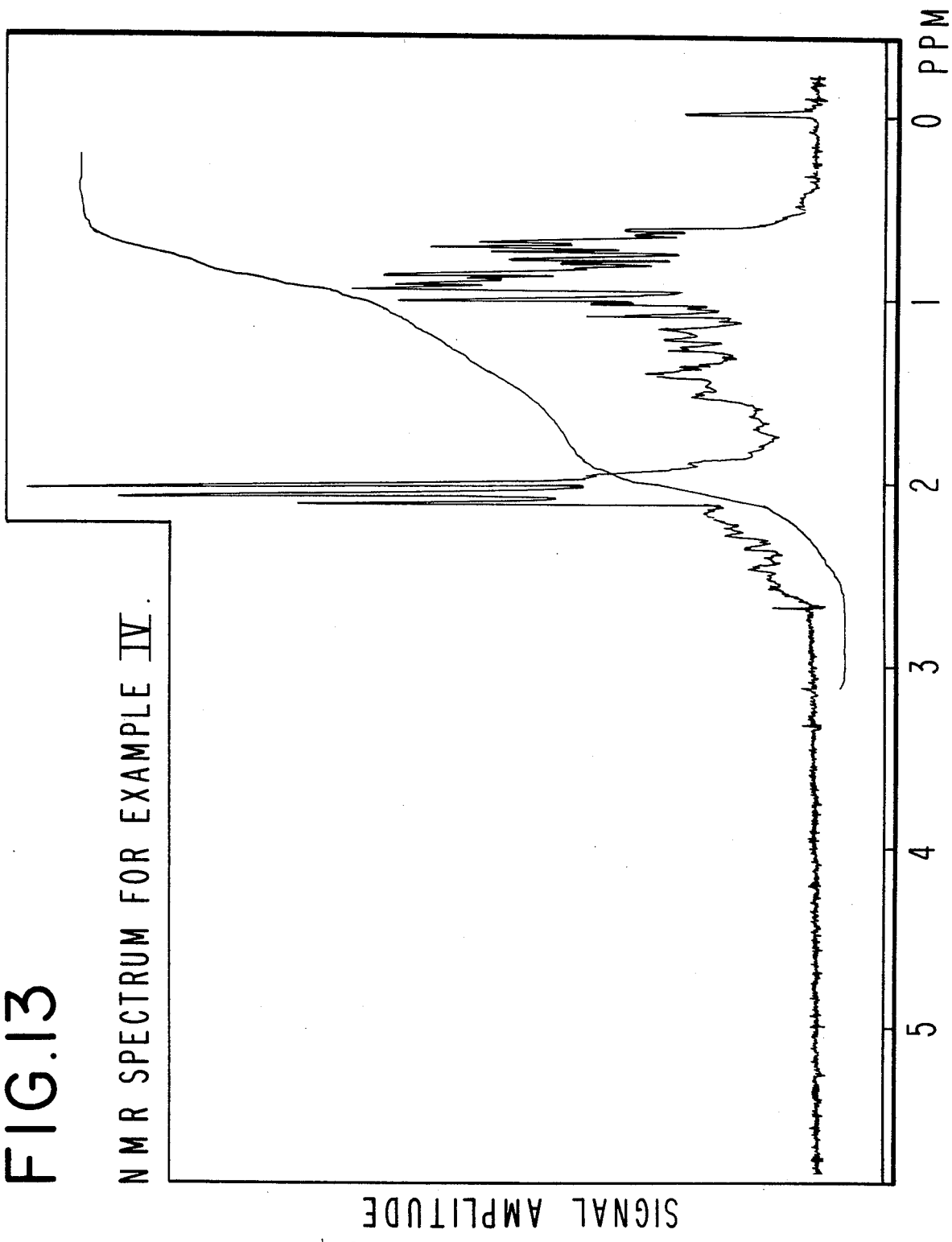

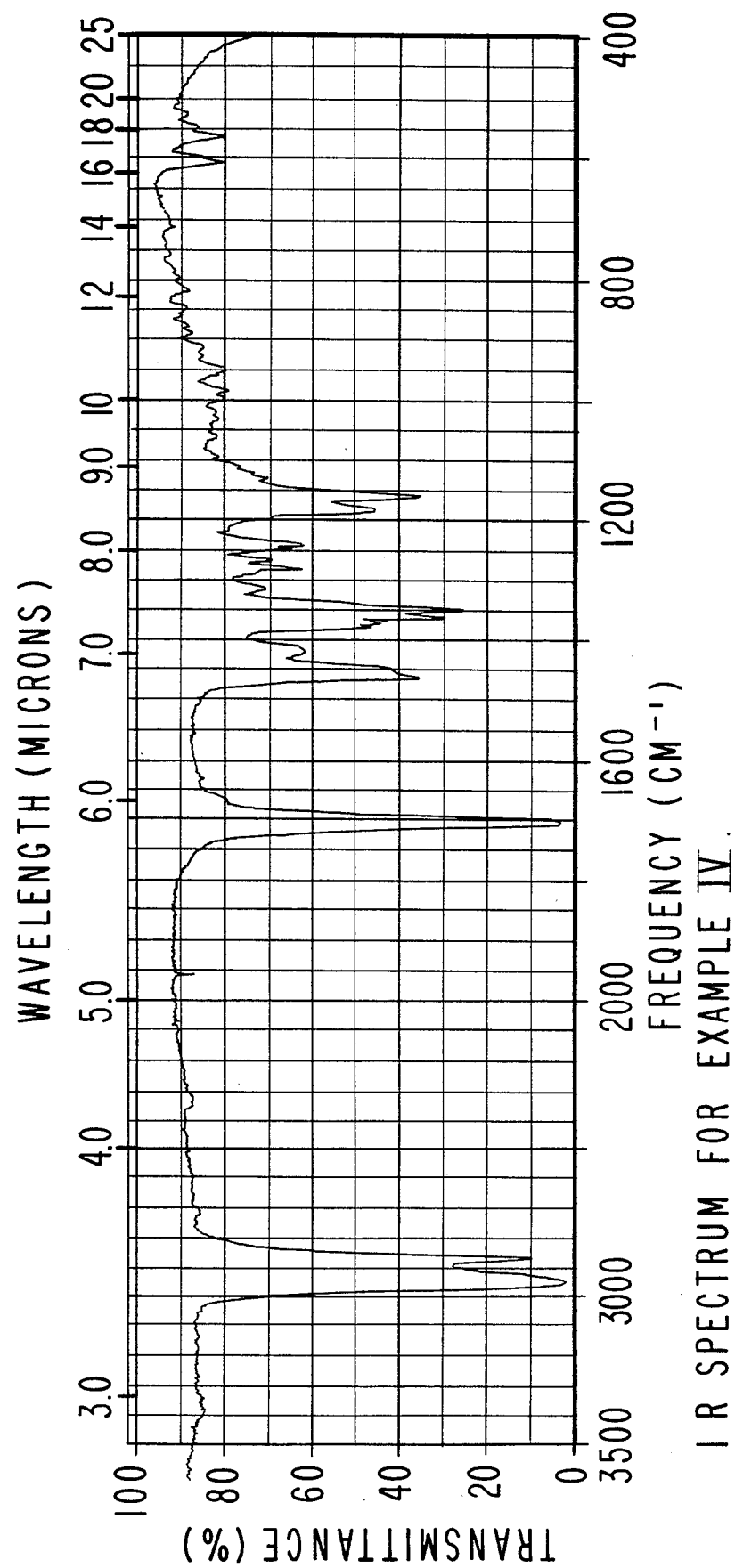

1-OXOALKYL-2-ISOPROPYLNORBORNANE DERIVATIVES, USES THEREOF IN AUGMENTING OR ENHANCING THE AROMA OF CONSUMABLE MATERIALS AND PROCESSES FOR PREPARING SAME

BACKGROUND OF THE INVENTION

The present invention relates to 1-oxoalkyl-2-isopropylnorbornane derivatives defined according to the structure:

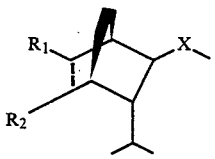

wherein X represents a moiety selected from the group consisting of:

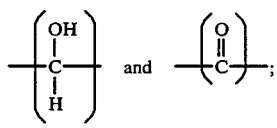

wherein the dashed line represents a carbon-carbon double bond or a carbon-carbon single bond and wherein $R_1$ and $R_2$ represent hydrogen or methyl with the proviso that $R_1$ and $R_2$ are not both methyl, and organoleptic uses thereof in perfumery.

Substances which provide sweet, herbaceous, minty, fruity, green, cucumber-like, rosy, cedarleaf-like, tobacco-like, sweaty, woody, camphoraceous, earthy and spicy aroma nuances with rosy, minty, herbaceous, dried-fruit, woody, sweaty, camphoraceous, earthy, piney, spicy, melony and fruity undertones are highly desirable in the art of perfumery. Many of the natural materials which provide such fragrances and contribute such desired nuances to perfumery compositions are high in cost, vary in quality from one batch to another and/or are generally subject to the usual variations of natural products.

There is, accordingly, a continuing effort to find synthetic materials which will replace, enhance or augment the essential fragrance notes provided by natural essential oils or compositions thereof. Unfortunately, many of the synthetic materials either have the desired nuances only to a relatively small degree or else contribute undesirable or unwanted odor to the compositions. The search for materials which can provide a more refined rose aroma or a more refined woody aroma, for example, has been difficult and relatively costly in the area of both natural products and synthetic products.

Alkyl substituted acetyl norbornene derivatives are known in the prior art for use in perfumery. Thus, U.S. Pat. No. 3,852,358 issued on Dec. 3, 1974 discloses the reaction of α,β unsaturated ketones with cyclopentadiene according to the reaction:

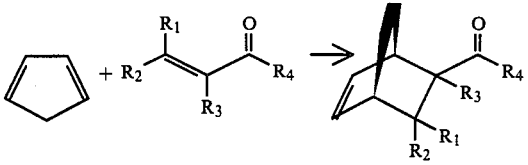

wherein $R_1$ and $R_4$ represent alkyl and one of $R_2$ and $R_3$ is alkyl and the other is hydrogen. Specifically U.S. Pat. No. 3,852,358 discloses the following reactions:

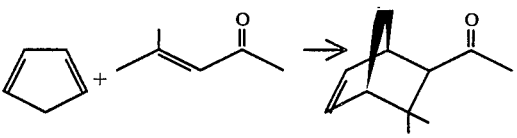

and

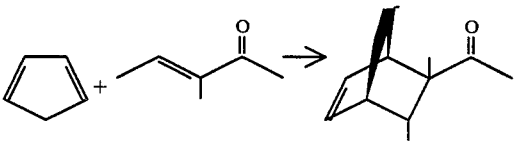

wherein the cyclopentadiene results from the cracking of bicyclopentadiene according to the reaction:

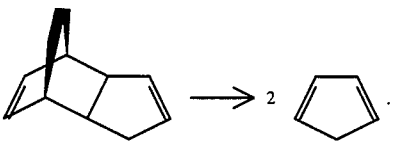

In the reaction of our invention the cracking of the bicyclopentadiene can take place in situ in view of the structures of the reactants and the resulting reaction products.

The compound having the structure:

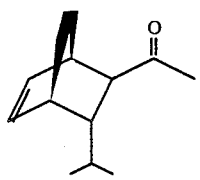

which is a member of the genus of 1-oxoalkyl-2-isopropylnorbornane derivatives useful in the practice of our invention is a known compound, disclosed in Chem.Abstracts, Vol. 82, 1975, No. 16237m (abstract of Bull. Chem. Soc., Jap. 1974, 47(7), 1673–7. Compounds of the genus:

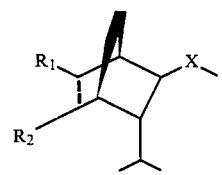

other than the compound having the structure:

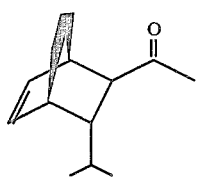

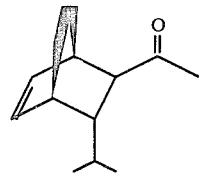

are novel compounds. Thus, the novel compounds of our invention are defined according to the structure:

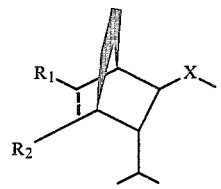

wherein X is a moiety selected from the group consisting of:

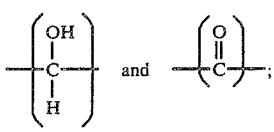

the dashed line represents a carbon-carbon single bond or a carbon-carbon double bond; $R_1$ and $R_2$ each represent hydrogen or methyl with the provisos:

(i) both $R_1$ and $R_2$ are not methyl;

(ii) when $R_1$ and $R_2$ each represent hydrogen and X is the moiety:

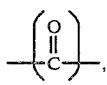

then the dashed line is a carbon-carbon single bond.

Nothing in the prior art suggests the 1-oxoalkyl-2-isopropylnorbornane derivatives of our invention as being useful in augmenting or enhancing the aroma of consumable materials selected from the group consisting of perfume compositions, colognes and perfumed articles.

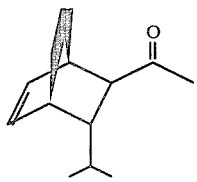

(mixture of "endo" and "exo" isomers).

Figure 2:
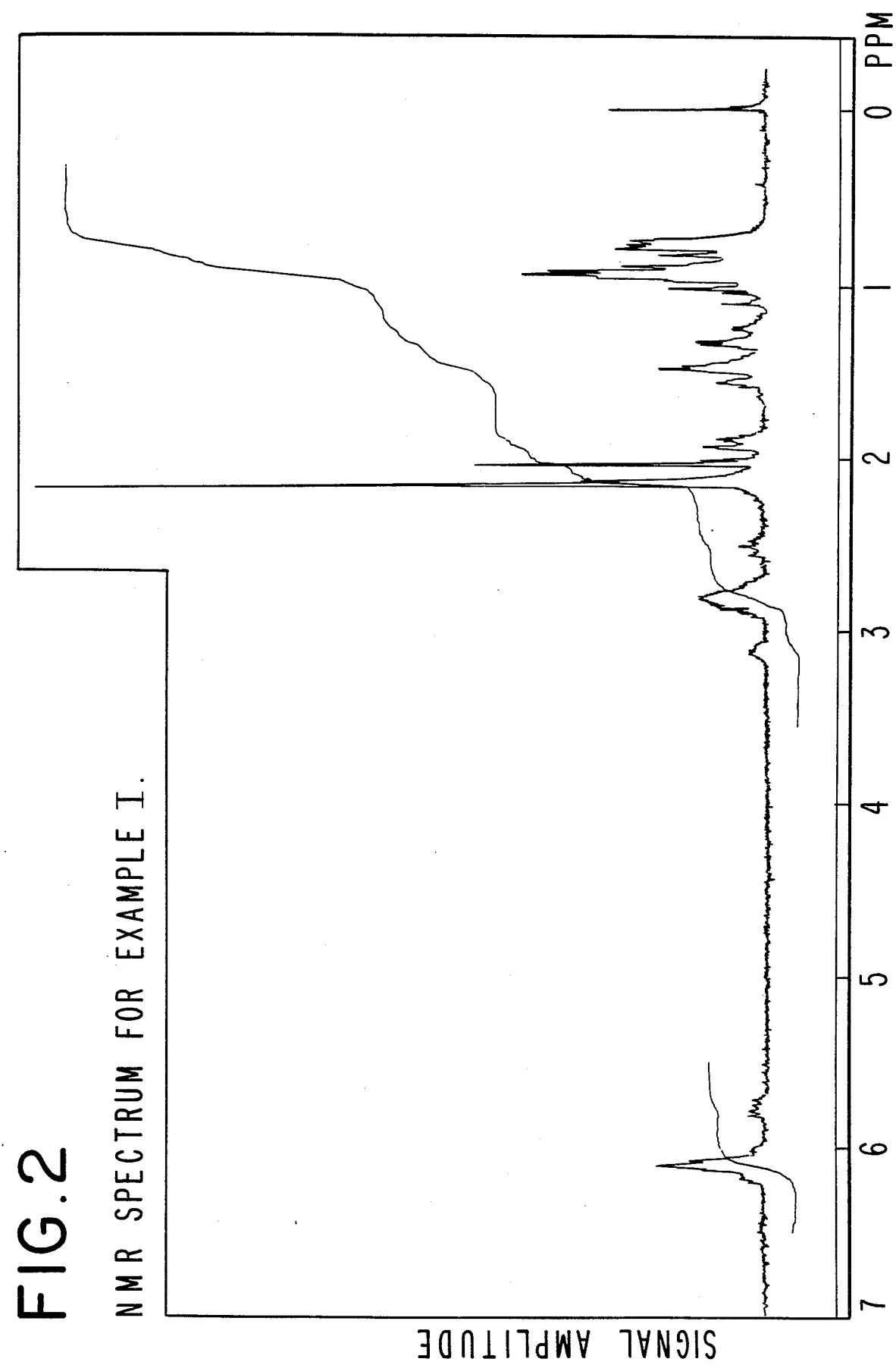

FIG. 2 is the NMR spectrum for the isomers of the compound having the structure:

("endo" and "exo" isomers) produced according to the first reaction of Example I (conditions: Field strength: 100 MHz; Solvent: CFCl₃).

Figure 3:
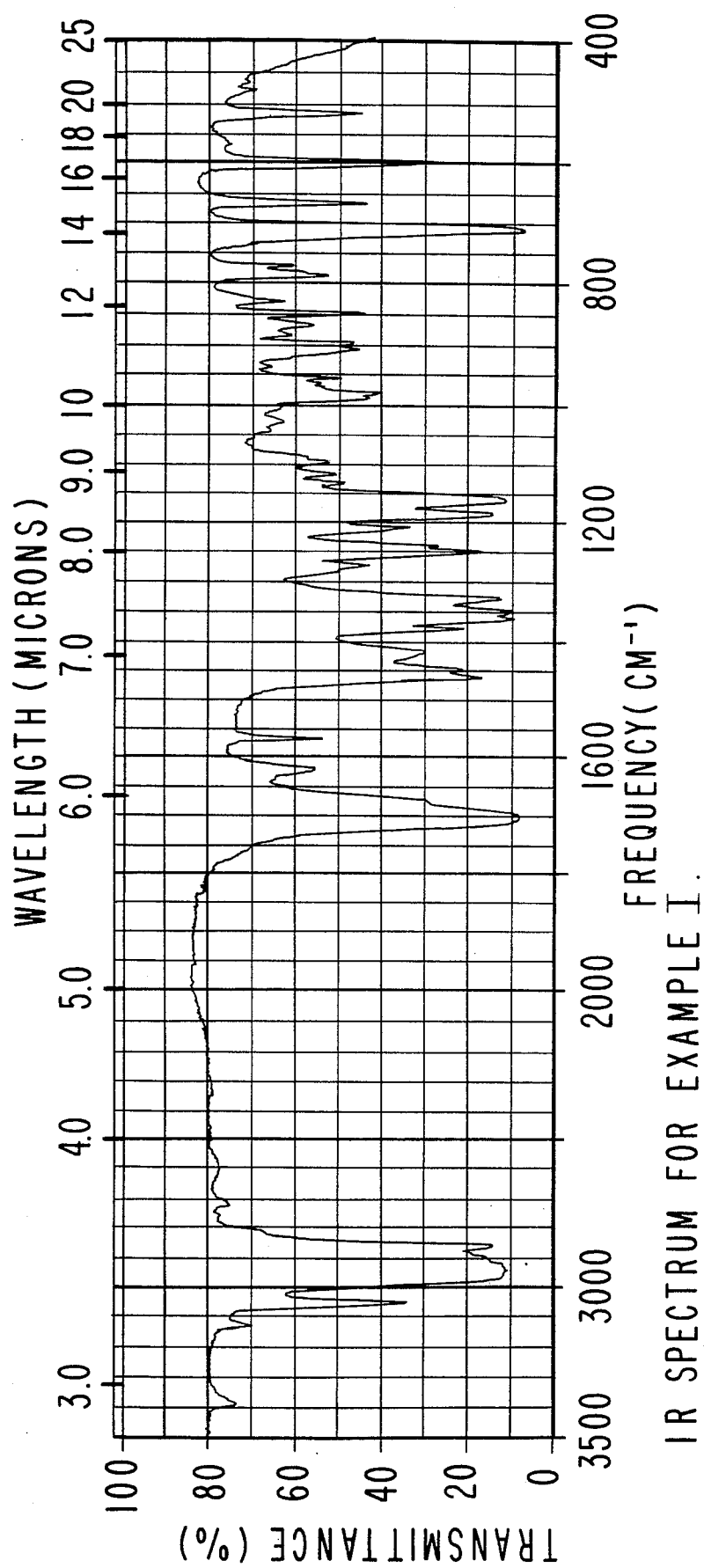

FIG. 3 is the infra-red spectrum for the compound having the structure:

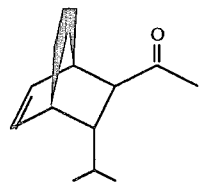

(mixture of "endo" and "exo" isomers) prepared according to Example I.

FIG. 4 is the NMR spectrum for the compound having the structure:

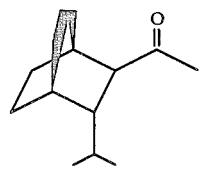

produced as a result of the second reaction of Example I (conditions: Field strength: 100 MHz; Solvent: CFCl₃).

FIG. 5 is the infra-red spectrum for the compound having the structure:

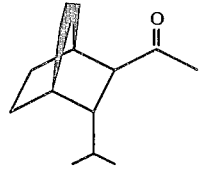

("endo" and "exo" isomers) produced according to the second reaction of Example I.

Figure 6:
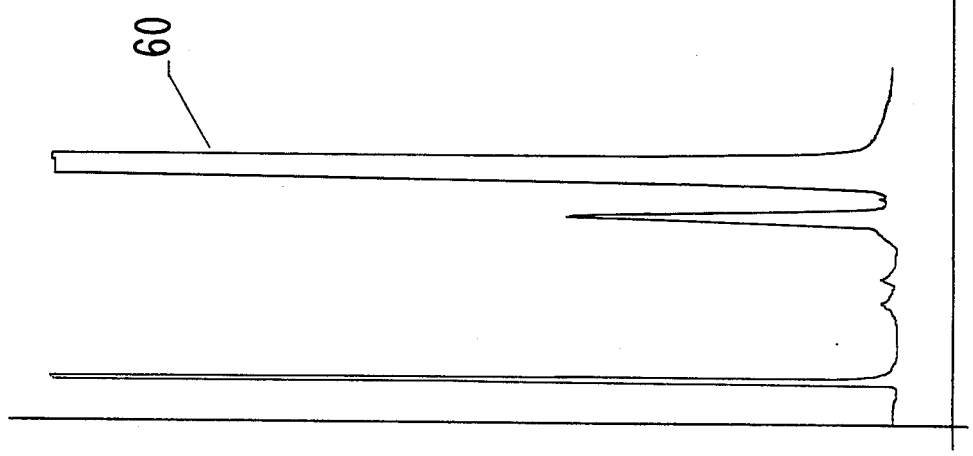

FIG. 6 is the GLC profile for the crude reaction product of Example II containing the compound defined according to the structure:

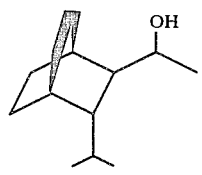

("exo" and "endo" isomers).

FIG. 7 is the NMR spectrum for the mixture of "endo" and "exo" isomers having the structure:

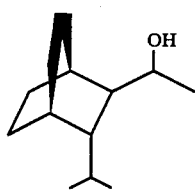

produced according to Example II.

Figure 8:
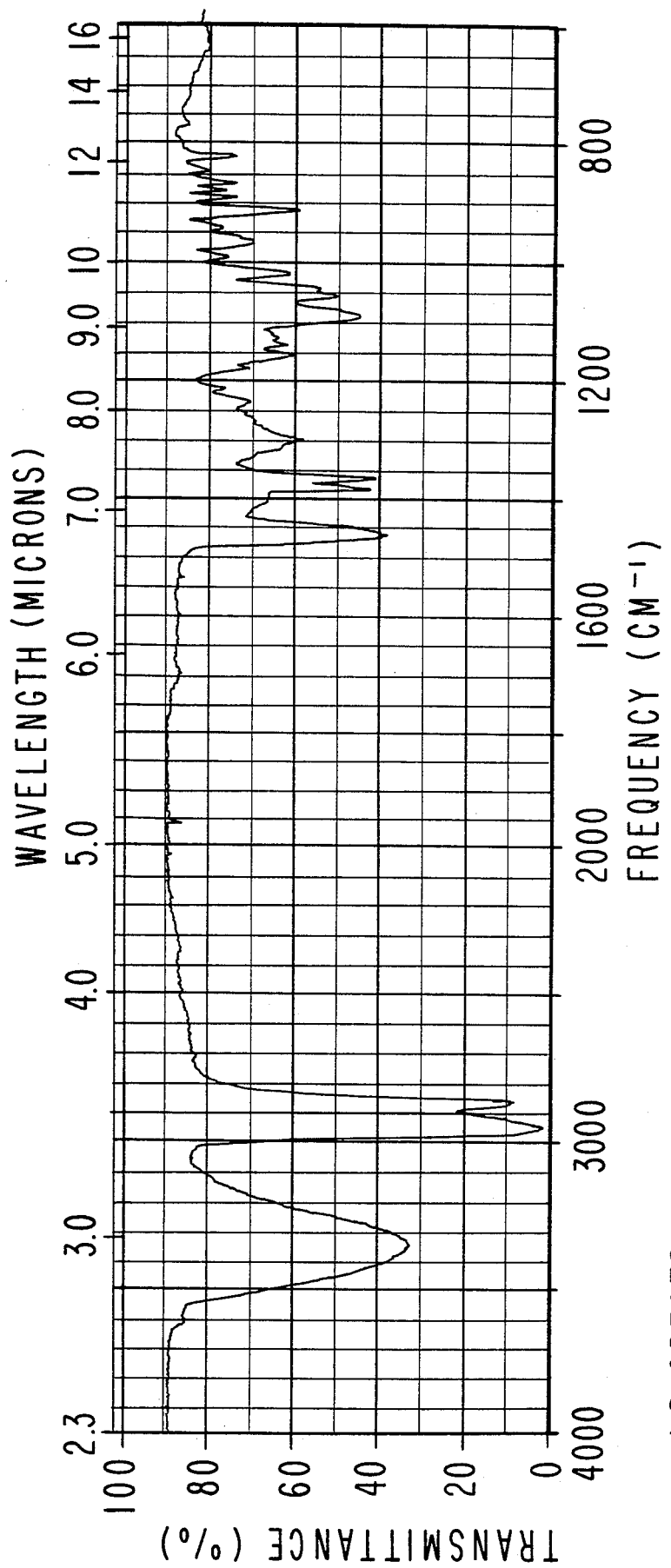

FIG. 8 is the infra-red spectrum for the mixture of "endo" and "exo" isomers having the structure:

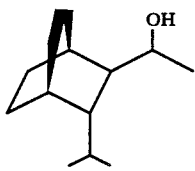

produced according to Example II.

Figure 9:
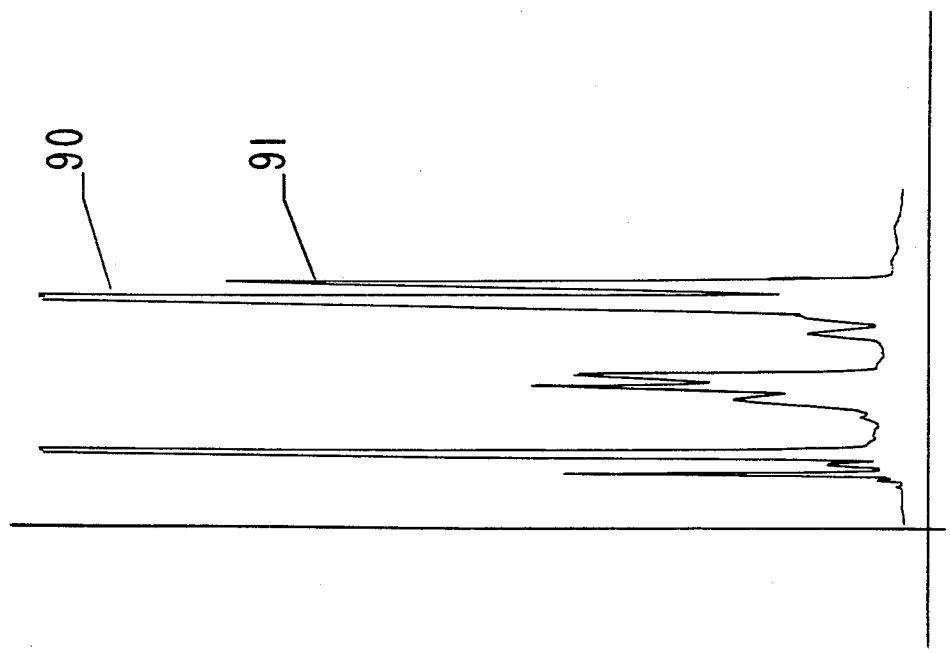

FIG. 9 is the GLC profile for the mixture of isomers (both "endo" and "exo" isomers) defined according to the structures:

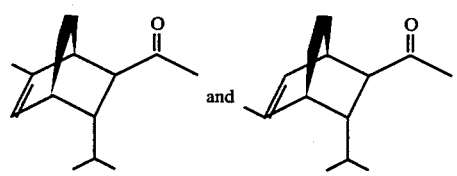

produced according to Example III.

Figure 10:
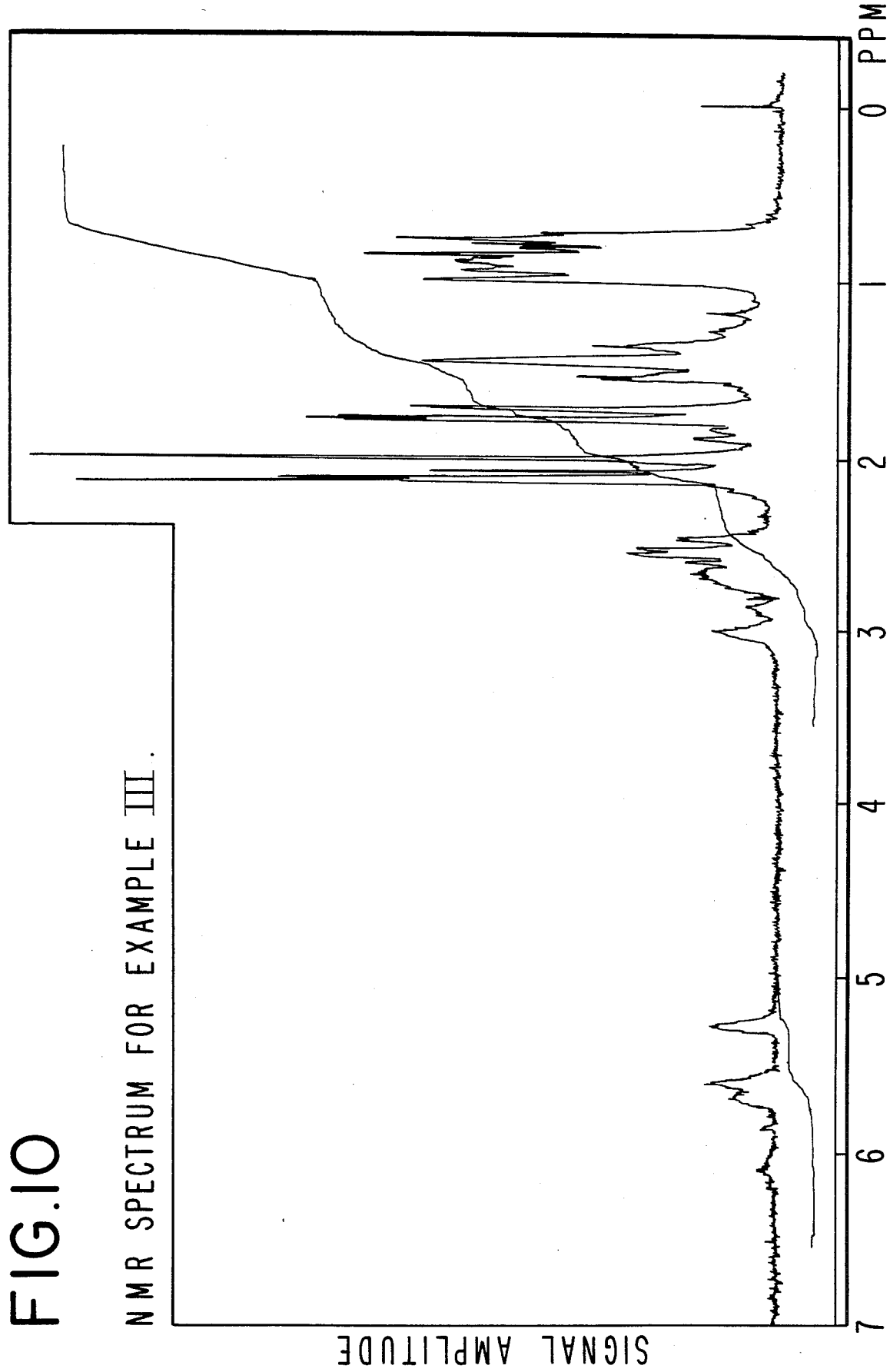

FIG. 10 is the NMR spectrum for the mixture of isomers having the structures:

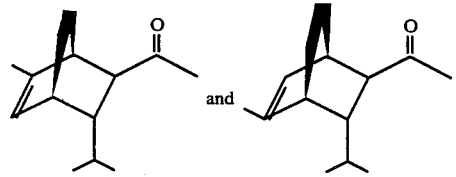

(mixtures of "exo" and "endo" isomers) produced according to Example III (conditions: Field strength: 100 MHz; Solvent: CFCl₃).

FIG. 11 is the infra-red spectrum for the mixture of compounds having the structures:

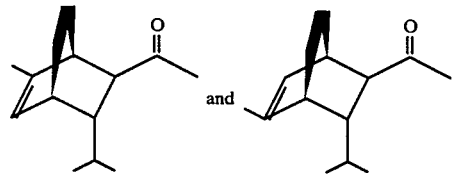

prepared according to Example III (mixtures of "endo" and "exo" isomers).

Figure 12:
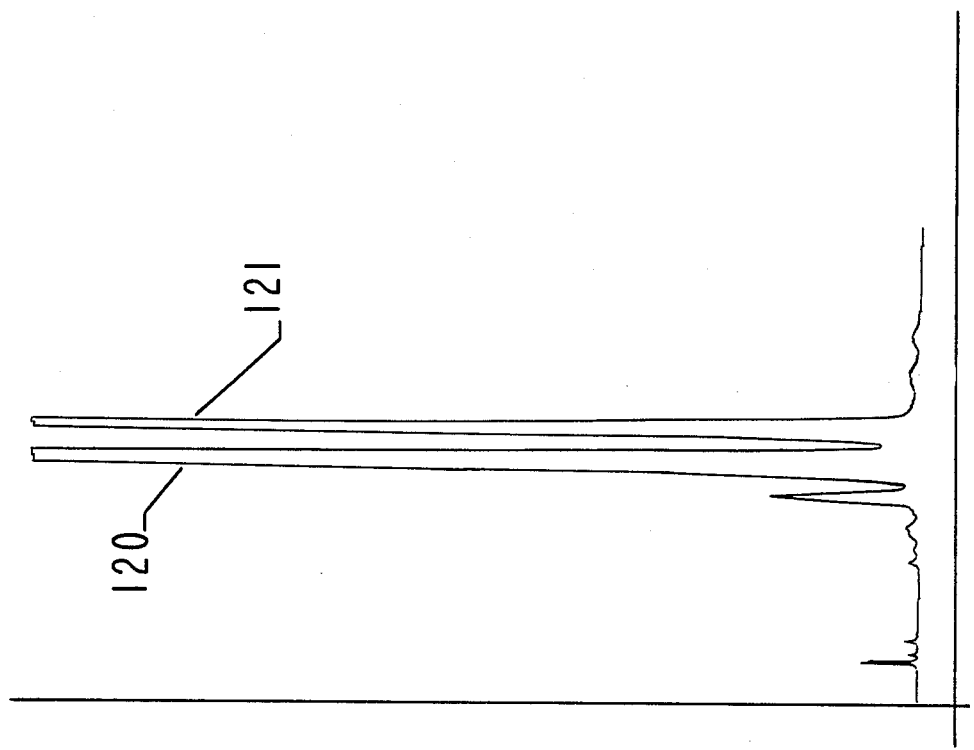

FIG. 12 is the GLC profile for the mixture of isomers having the structures:

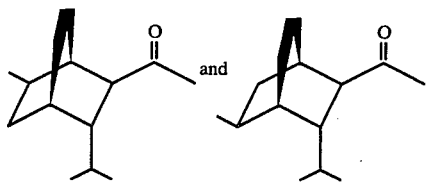

prepared according to Example IV (mixtures of "endo" and "exo" isomers).

FIG. 13 is the NMR spectrum for the mixture of isomers having the structures:

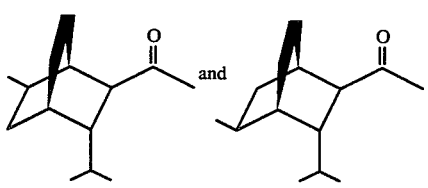

prepared according to Example IV (mixtures of "endo" and "exo" isomers). (Conditions: Solvent: CFCl₃; Field Strength: 100 MHz).

FIG. 14 is the infra-red spectrum for the mixture of isomers having the structures:

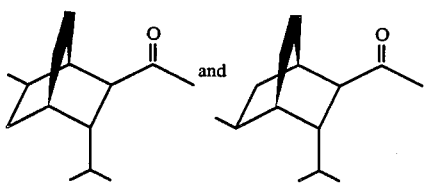

prepared according to Example IV (mixtures of "endo" and "exo" isomers).

Figures 15, 16:
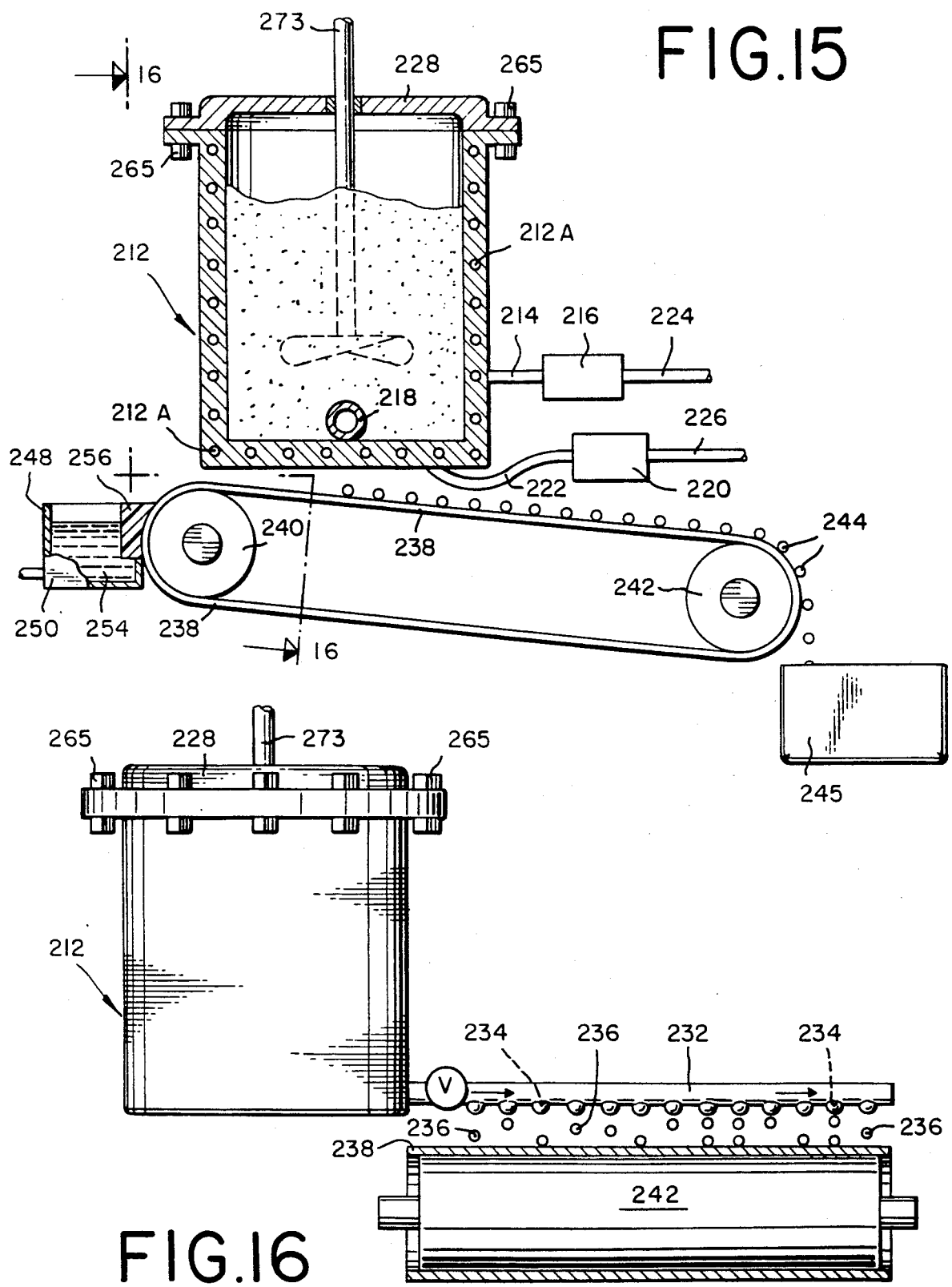

FIG. 15 is a cut-away side elevation view of apparatus used in preparing perfume containing polymers of our invention.

FIG. 16 is a cross sectional view taken along lines 16—16 of FIG. 15.

DETAILED DESCRIPTION OF THE DRAWINGS

Figure 1:
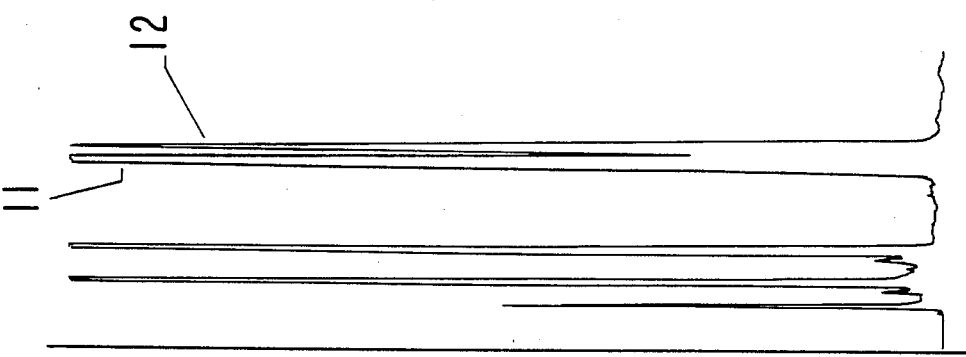
FIG. 1 is the GLC profile for the reaction product of the first reaction of Example I containing the product having the structure.

FIG. 1 is the GLC profile of the mixture of isomers prepared according to Example I (crude reaction product). The peaks indicated by reference numerals "11" and "12" are peaks for the "endo" and "exo" isomers of the compound having the structure:

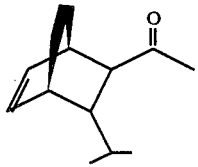

specifically compounds defined according to the structures:

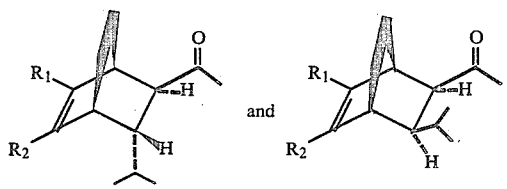

wherein R₁ and R₂ are each hydrogen.

FIG. 6 is the GLC profile for the crude reaction product of Example II containing the compound having the structure:

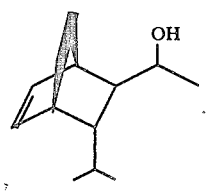

The peak indicated by reference numeral "60" is the peak for the mixture of "exo" and "endo" isomers having the structure:

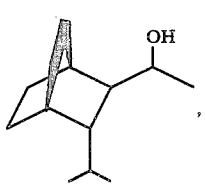

specifically,

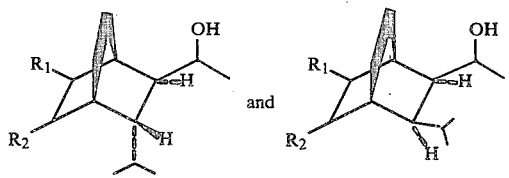

wherein R₁ and R₂ each represent hydrogen. (Conditions: Carbowax column programmed at 180° C. isothermal).

FIG. 9 is the GLC profile for the reaction product of Example III containing the compounds having the structures:

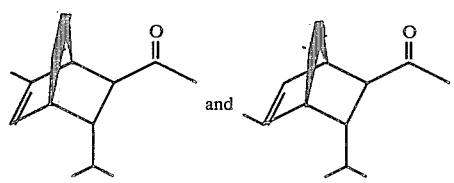

("exo" and "endo" isomers). The peaks indicated by reference numerals "90" and "91" are the peaks indicating the mixtures of "endo" and "exo" isomers of the compounds having the structures:

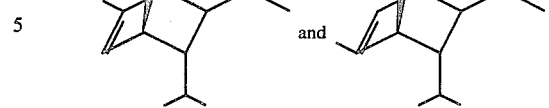

specifically, those isomers defined according to the structures:

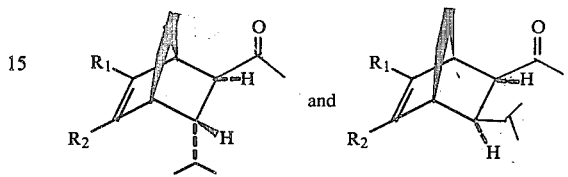

wherein one of R₁ or R₂ is methyl and the other of R₁ or R₂ is hydrogen. (Conditions: SE-30 column programmed at 150° C. isothermal).

FIG. 12 is the GLC profile for the crude reaction product of Example IV containing the "exo" and "endo" isomers of compounds having the structures:

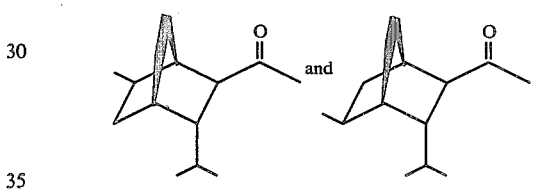

(Conditions: SE-30 column programmed at 180° C. isothermal). The peaks indicated by reference numerals "120" and "121" are peaks for the "endo" and "exo" isomers of the compounds having the structures:

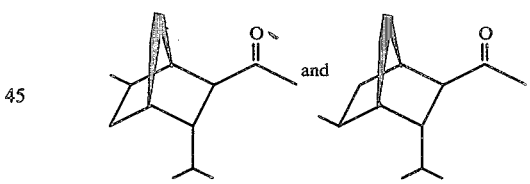

specifically, isomers defined according to the structures:

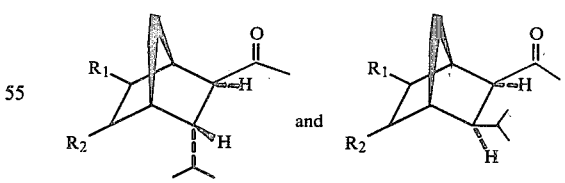

wherein one of R₁ or R₂ is methyl and the other of R₁ or R₂ is hydrogen.

Referring to FIGS. 15 and 16, a thermoplastic polymer, e.g., polyethylene is heated to about 220°–250° F. in a container 212 of the kind illustrated in FIGS. 15 and 16. A fragrance formulation, containing at least one of the 1-oxoalkyl-2-isopropylnorbornane derivatives defined according to the structure:

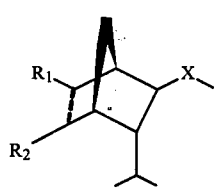

wherein the dashed line represents a carbon-carbon double bond or a carbon-carbon single bond and wherein $R_1$ and $R_2$ represent hydrogen or methyl with the proviso that $R_1$ and $R_2$ are not both methyl is then quickly added to the liquified thermoplastic polymer, the lid 228 is put in place and the agitating means 273 are actuated. The temperature is maintained at about 225° F. and the mixing is continued for about 5-15 minutes. The valve "V" is then opened to allow flow of the molten thermoplastic polymer enriched with the fragrance containing the compounds defined according to the structure:

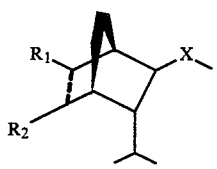

wherein the dashed line represents a carbon-carbon double bond or a carbon-carbon single bond and wherein $R_1$ and $R_2$ represent hydrogen or methyl with the proviso that $R_1$ and $R_2$ are not both methyl to exit through the orifices 234. The liquid falling through the orifices 234 solidifies almost instantaneously upon impact with moving cooled conveyor 238. The thermoplastic polymer beads or pellets 224 having pronounced aromas as described, supra and infra (e.g., a rose aroma) are thus formed. These pellets are further utilized as set forth in specific examples, infra.

THE INVENTION

This invention relates to 1-oxoalkyl-2-isopropylnorbornane derivatives defined according to the structure:

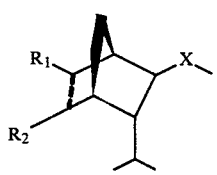

wherein X represents a moiety selected from the group consisting of:

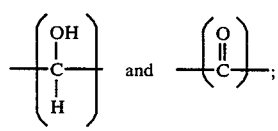

wherein the dashed line represents a carbon-carbon double bond or a carbon-carbon single bond and wherein $R_1$ and $R_2$ represent hydrogen or methyl with the proviso that $R_1$ and $R_2$ are not both methyl, for augmenting or enhancing the aroma of consumable materials including perfume compositions, colognes and perfumed articles. The 1-oxoalkyl-2-isopropylnorbornane derivatives defined according to the structure:

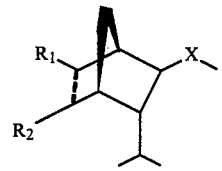

also include "endo" and "exo" isomers, for example, the isomers having the structures:

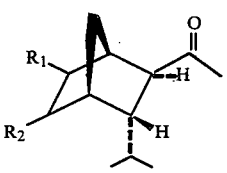 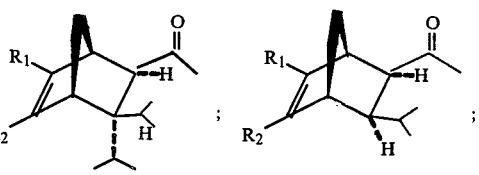

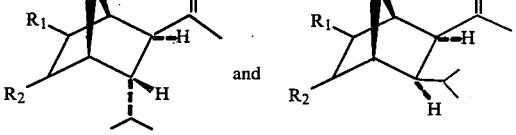

Briefly, our invention contemplates augmenting or enhancing the fragrances of such consumable materials as perfumes, perfumed articles (e.g., solid or liquid anionic, cationic, nonionic or zwitterionic detergents, cosmetic powders, hair preparations such as shampoos and perfumed thermoplastic and thermoset resins) and colognes by adding thereto a small but effective amount of at least one of the 1-oxoalkyl-2-isopropylnorbornane derivatives of our invention defined according to the structure:

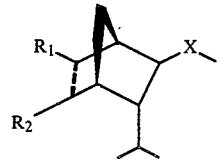

wherein the dashed line represents a carbon-carbon double bond or a carbon-carbon single bond and wherein $R_1$ and $R_2$ represent hydrogen or methyl with the proviso that $R_1$ and $R_2$ are not both methyl.

The 1-oxoalkyl-2-isopropylnorbornane derivatives of our invention augment or enhance or impart sweet, herbaceous, minty, fruity, green, cucumber-like, rosy, cedarleaf-like, tobacco-like, sweaty, woody, camphoraceous, earthy and spicy aroma nuances with strong rosy, minty, herbaceous, dried fruit, woody, sweaty, camphoraceous, earthy, piney, spicy, melony and fruity undertones.

Depending upon the method and reactants used to prepare the 1-oxoalkyl-2-isopropylnorbornane derivatives of our invention having the structure:

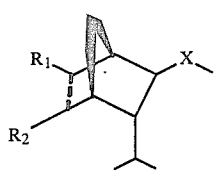

wherein the dashed line represents a carbon-carbon double bond or a carbon-carbon single bond and wherein $R_1$ and $R_2$ represent hydrogen or methyl with the proviso that both $R_1$ and $R_2$ are not both methyl, the aroma nuances of the resulting isomer mixture will differ in a number of respects.

The 1-oxoalkyl-2-isopropylnorbornane derivatives of our invention can be produced according to one of two techniques:

a. by means of a Diels Alder reaction of 2-methyl-3-hexen-5-one with a bicyclopentadiene according to the reaction:

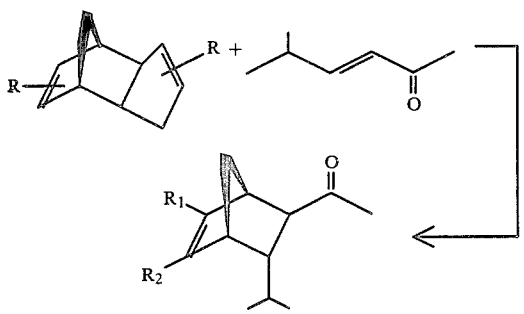

wherein $R_1$ and $R_2$ each represent hydrogen or methyl with the proviso that at least one of $R_1$ or $R_2$ is hydrogen at a pressure in the range of from about 20 psig up to about 300 psig and at a temperature in the range of from about 130° C. up to about 200° C. thereby yielding a mixture of "exo" and "endo" isomers which can be used as is for its perfumery properties or which can be further reacted as by means of reaction with hydrogen over a catalyst such as palladium on carbon or palladium on calcium carbonate or palladium on barium sulfate or by means of a reduction reaction using an alkali metal borohydride such as sodium borohydride; and b. by means of the above Diels Alder reaction being operated at lower temperatures in the presence of a Lewis acid catalyst according to the conditions of U.S. Pat. No. 3,852,358.

A bicyclopentadiene utilized should be relatively pure, preferably more than 95% pure to assure high conversion. All parts, percentages, proportions and ratios herein are by weight unless otherwise indicated. It is generally desirable to carry out the reaction in the presence of a liquid reaction vehicle. The vehicle is preferably a solvent for the reactants and catalyst system utilized and such vehicles have been found to improve yields markedly in the catalytic reaction while affording good control over the reaction. Preferred reaction vehicles include halogenated hydrocarbons, desirably chlorinated lower hydrocarbons such as methylene chloride, chloroform, and the like, and aromatic hydrocarbons, particularly halogenated mononuclear aromatic hydrocarbons, such as dichlorobenzene, and the like, and mononuclear aromatic alkylated liquids such as toluene, xylene and the like. The quantity of vehicle utilized can range from none to about 300 g for each mole of bicyclopentadiene in the reaction mixture. It is preferred to use from about 100 g to 250 g of vehicle for each mole of the diene.

The catalysts found suitable for use in the process of the present invention are Lewis acid halide materials. The preferred catalysts include aluminum chloride, stannic chloride, bismuth trichloride, titanium tetrachloride, ferric chloride, and boron trihalide, such as boron trifluoride and boron trifluoride etherate, ethyl aluminum dichloride, diethyl aluminum chloride, bismuth trichloride, antimony trichloride and the like. It will be appreciated by those skilled in the art from the present disclosure that adducts of such Lewis acid catalysts, for example, boron trifluoride etherate are also intended to be included within the aforesaid catalysts.

The quantity of catalyst varies depending upon the particular reactants, the reaction vehicle, the temperature and time of the reaction, and the particular catalyst or combination thereof used. For example, it has been found that certain embodiments of the invention utilize approximately four times as much titanium tetrachloride as is required with aluminum chloride catalyst. Broadly, the amount of catalyst can be present in a ratio of from 0.005 moles to about one mole of catalyst for each mole of bicyclopentadiene. Generally, however, modest amounts of catalyst of the order of from about 0.02 up to about 0.05 moles per mole of the diene are preferred.

The ratio of the bicyclopentadiene to the dienophile which is in this case 2-methyl-3-hexen-5-one can be above, below, or equal to the stoichiometric amount, but generally economy in certain embodiments of the processes make approximately stoichiometric amounts desirable. It is preferred in many embodiments of the invention that the compound, the 2-methyl-3-hexen-5-one be present in an amount of from about equimolar up to about a 20 percent molar excess over the bicyclopentadiene or methyl bicyclopentadiene derivative.

One of the outstanding advantages of the present process is the modest temperatures required to achieve good yields of "exo" isomer and satisfactory reaction times. The "exo" isomers produced according to our invention are shown thusly:

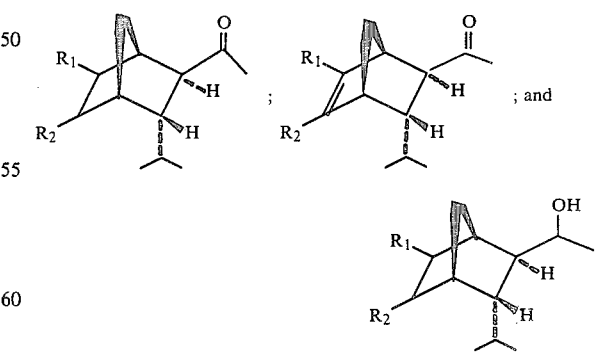

Obviously, the resulting product from the catalytic Diels Alder reaction can be utilized as is or it can be subsequently reduced as by hydrogenation, or using an alkali metal borohydride as further described, in detail, infra.

One of the outstanding advantages of the present catalytic process is the modest temperature required to achieve good yields and satisfactory reaction times. Generally, the temperature is in the range of from about 0° C. up to about 50° C. when carrying out the catalytic Diels Alder reaction and in a preferred embodiment of the invention the temperature is from about 15° C. up to about 30° C. Even at these modest temperatures, the reaction times are on the order of from about one up to about 10 hours and it is generally preferred to carry the reaction for from about 3 up to about 6 hours.

The reaction of this invention can be carried out over a range of pressures, but since the process does not require special high-pressure techniques like those of the thermal reaction cited, supra, it is especially preferred to conduct the reaction at atmospheric pressure. Another of the advantages of the present invention is the freedom in admixing reagents. It is possible to use any combination of sequential or simultaneous addition of the bicyclopentadiene, the 2-methyl-3-hexen-5-one and the catalyst. It has been found desirable in obtaining the highest possible yields sequentially to add first the 2-methyl-3-hexen-5-one and then the bicyclopentadiene to the Lewis acid catalyst.

The resulting product from the process can be washed with salt solutions, acids and/or bases to remove reaction products and to provide an initial cleansing of the product. The resulting cyclic product defined generically according to the structure:

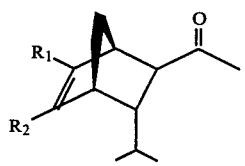

wherein $R_1$ and $R_2$ represent hydrogen or methyl with the proviso that at least of one $R_1$ or $R_2$ is hydrogen is recovered from the reaction mixture and can then be subjected to conventional purification and/or isolation techniques such as distillation, crystallization, extraction, preparative chromatographic techniques and the like. It is especially preferred to purify the materials by vacuum distillation, and adjuvant materials such as antioxidants, petroleum base oils, trialkanolamines and the like can be used.

When it is desired to reduce the resulting ketones defined according to the structure:

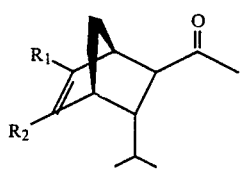

the reduction can be carried out with hydrogen in the presence of a hydrogenation catalyst such as palladium on carbon, palladium on calcium carbonate and palladium on barium sulfate. When such a reaction is carried out the double bond in the ring is reduced to a single bond but the ketone moiety is not caused to be reduced thereby forming the generic structure:

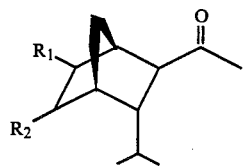

according to the reaction:

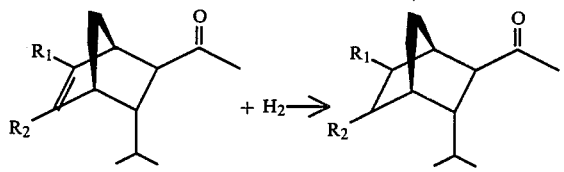

The hydrogenation reaction is carried out at a temperature in the range of from about 20° C. up to about 80° C. at a pressure in the range of from about 40 psig up to about 400 psig.

In the alternative, the resulting compounds defined according to the structure:

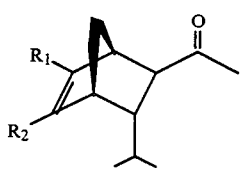

may be reduced using an alkali metal borohydride whereby the double bond within the norbornene ring is not reduced but the ketone moiety is reduced to an alcohol according to the reaction:

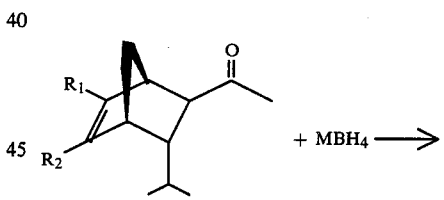

Such a reaction is carried out using an alkali metal borohydride such as sodium, potassium or lithium borohydride. The reaction conditions for carrying out this reduction are well known to those skilled in the art. The reaction is carried out in the presence of a solvent which is inert to the reaction mass such as isopropyl alcohol, the solvent being required to have such a volatility that the reaction mass may be refluxed at a temperature in the range of from about 60° C. up to about 100° C.

Under the same conditions, the genus of compounds having the structure:

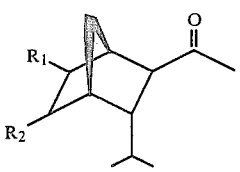

may be reduced to the corresponding alcohols having the structure:

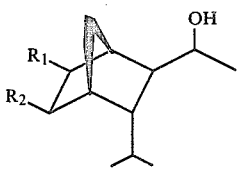

also using an inert solvent and an alkali metal borohydride catalyst according to the reaction:

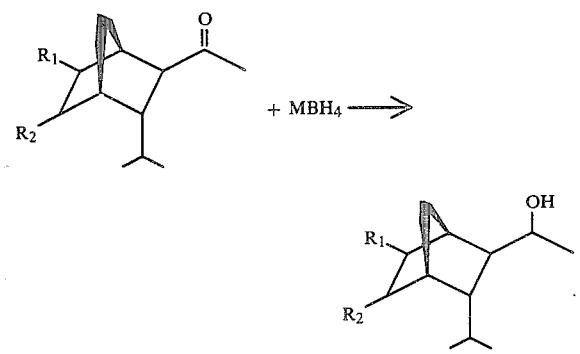

Table I set forth below indicates the various reaction products of our invention and their specific organoleptic properties insofar as perfumery properties are concerned.

TABLE I

| Structure of Compounds Produced by Processes of Our Invention | Organoleptic Properties |
|---|---|
| A mixture of "endo" and "exo" isomers having the structure:<br>[structure] | A sweet herbaceous, minty, fruity, green and cucumber-like aroma profile. |
| A mixture of "exo" and "endo" isomers having the structure:<br>[structure] | A strong, herbaceous, fruity, rosy, cedarleaf-like and tobacco-like aroma with rosy, minty, herbaceous and dried fruit undertones. |
| A mixture of compounds having the structure:<br>[structure]<br>("exo" and "endo" isomers). | A minty, sweaty, woody, camphoraceous and earthy aroma profile with woody, minty, sweaty, camphoraceous and earthy undertones. |

TABLE I-continued

| Structure of Compounds Produced by Processes of Our Invention | Organoleptic Properties |
|---|---|
| A mixture of "exo" and "endo" isomers having the structures:<br>[structure]<br>and<br>[structure] | A herbaceous, spicy, green, rosy and fruity aroma profile with piney, minty, rosy, spicy, melony and fruity undertones. |
| A mixture of "exo" and "endo" isomers of chemicals having the structures:<br>[structure]<br>and<br>[structure]<br>produced according to Example IV. | A woody and camphoraceous aroma profile. |

Thus, an olfactory agents, the 1-oxoalkyl-2-isopropylnorbornane derivatives of our invention can be formulated into or used as components of a "perfume composition".

The term "perfume composition" is used herein to mean a mixture of organic compounds including, for example, alcohols other than the alcohols of our invention, aldehydes, ketones other than the ketones of our invention, nitriles, ethers, lactones, and frequently hydrocarbons which are admixed so that the combined odors of the individual components produce a pleasant or desired fragrance. Such perfume compositions usually contain (a) the main note or the "bouquet" or foundation stone of the composition; (b) modifiers which round off and accompany the main note; (c) fixatives which include odorous substances which lend a particular note to the perfume throughout all stages of evaporation and substances which retard evaporation and (d) topnotes which are usually low-boiling, fresh-smelling materials.

In perfume compositions, the individual component will contribute its particular olfactory characteristics, but the overall effect of the perfume composition will be the sum of the effects of each of the ingredients. Thus, the individual compounds of this invention or mixtures thereof, can be used to alter the aroma characteristics of a perfume composition, for example, by highlighting or moderating the olfactory reaction contributed by another ingredient in the composition.

The amount of the 1-oxoalkyl-2-isopropylnorbornane derivatives of our invention which will be effective in perfume compositions depends on many factors including the other ingredients, their amounts and the effects which are desired. It has been found that perfume compositions containing as little as 0.5% of one or more of the 1-oxoalkyl-2-isopropylnorbornane derivatives of our invention or even less, can be used to impart an interesting sweet, herbaceous, minty, fruity, green, cucumber-like, rosy, cedarleaf-like, tobacco-like, sweaty, woody, camphoraceous, earthy and spicy aromas with rosy, minty, herbaceous, dried-fruit, woody, sweaty, camphoraceous, earthy, piney, spicy, melony and fruity undertones to soaps, cosmetics and other products including solid or liquid anionic, cationic, nonionic or zwitterionic detergents and perfumed plastics. The amount employed can range up to 50% or higher and will depend on considerations of cost, nature of the end product and the effect desired on the finished product and the particular fragrance sought.

The 1-oxoalkyl-2-isopropylnorbornane derivatives of our invention can be used alone or in a perfume composition as an olfactory component in detergents and soaps, space odorants and deodorants; perfumes, colognes, toilet water, bath salts; hair preparations such as lacquers, brilliantines, pomades and shampoos; cosmetic preparations such as creams, deodorants, hand lotions and sun screens; powders such as talcs, dusting powders, face powders and the like. When used as an olfactory component for perfumed articles, as little as 0.01% of the 1-oxoalkyl-2-isopropylnorbornane derivatives of our invention will suffice to impart a sweet, herbaceous, minty, fruity, green cucumber-like, rosy, cedarleaf-like, tobacco-like, sweaty, woody, camphoraceous, earthy and spicy aromas with rosy, minty, herbaceous, dried-fruit, woody, sweaty, camphoraceous, earthy, piney, spicy, melony and fruity undertones. Generally no more than 0.8% based on the weight of the perfumed article is required. Thus, the range of use of the 1-oxoalkyl-2-isopropylnorbornane derivatives of our invention in perfumed articles is from about 0.01% up to about 0.8%.

In addition, the perfume composition can contain a vehicle or carrier for the 1-oxoalkyl-2-isopropylnorbornane derivatives of our invention, taken alone or taken further together with other ingredients. The vehicle can be a liquid such as an alcohol such as ethanol, a glycol such as propylene glycol or the like. The carrier can be an absorbent solid such as a gum (e.g., guar gum or xanthan gum) or components for encapsulating the composition such as gelatin (as by coacervation) or a urea formaldehyde polymer (for forming polymerized capsules around the central perfume oil cores each of which is located within a particular capsule).

The following examples are given to illustrate embodiments of this invention as it is presently preferred to practice it. It will be understood that these examples are illustrative and that the invention is not to be considered as restricted thereto except as indicated in the appended claims.

EXAMPLE I

FORMATION OF ACETYL ISOPROPYLNORBORNENE AND ACETYL ISOPROPYLNORBORNANE

Reactions:

A.

-continued
Reactions:

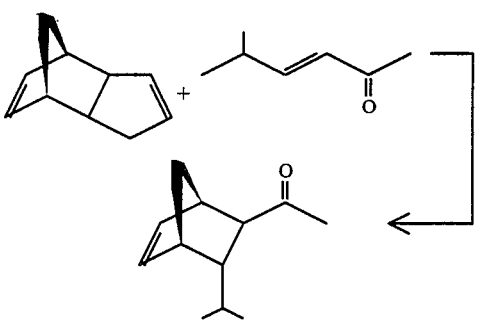

B.

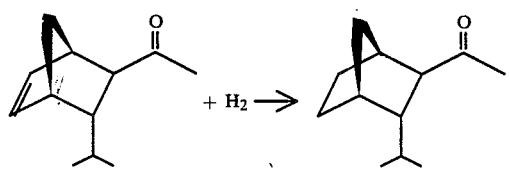

Into a pressure autoclave is placed 396 grams (3 moles) of dicyclopentadiene and 576 grams (6 moles) of 2-methyl-3-hexen-5-one. The autoclave is sealed and heated to 150° C. (pressure: 180 psig) and maintained at 150° C. and 180° C. psig for a period of 1.5 hours. At the end of the 1.5 hour period, the autoclave is opened and the contents are fractionally distilled yielding the following fractions:

| Fraction No. | Vapor Temp. (°C.) | Liquid Temp. (°C.) | Vacuum mm/Hg. Mercury |
|---|---|---|---|
| 1 | 23/68 | 23/78 | 200/100 |
| 2 | 68 | 78 | 100 |
| 3 | 82 | 92 | 100 |
| 4 | 93 | 109 | 60 |
| 5 | 101 | 112 | 60 |
| 6 | 95 | 110 | 104 |
| 7 | 96 | 110 | 4 |
| 8 | 100 | 120 | 4 |
| 9 | 135 | 185 | 16 |

FIG. 1 is the GLC profile of the crude reaction product prior to the distillation, containing the compound having the structure:

The peaks indicated by reference numerals "11" and "12" are for the "endo" and "exo" isomers of this compound having the structures:

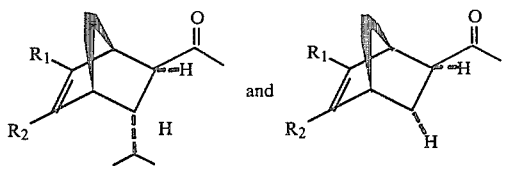

wherein $R_1$ and $R_2$ each represent hydrogen.

Bulked fractions 6-8 has a sweet, herbaceous, minty, fruity, green cucumber-like aroma profile.

FIG. 2 is the NMR spectrum for the mixture of "endo" and "exo" isomers having the structure:

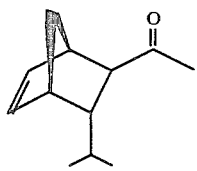

(conditions: Field strength: 100 MHz; Solvent: $CFCl_3$).

FIG. 3 is the infra-red spectrum for the mixture of isomers having the structure:

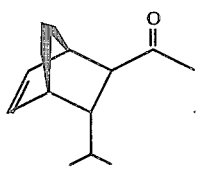

Distillation fractions 2-8 are bulked and placed in an autoclave equipped with a hydrogen gas feed line. Five grams of 5% palladium on carbon catalyst is placed into the autoclave along with 300 grams of distillation product. The autoclave is sealed and pressurized with hydrogen to 50 psig at a temperature of 30° C. The autoclave is maintained at 30° C. and 50 psig for a period of seven hours. At the end of the seven-hour period, the autoclave is opened and the product is filtered. The resulting filtrate is then fractionally distilled yielding the following fractions:

| Fraction No. | Vapor Temp. (°C.) | Liquid Temp. (°C.) | Vacuum mm/Hg. Mercury |
|---|---|---|---|
| 1 | 23/30 | 23/110 | 200/6 |
| 2 | 72 | 93 | 4.0 |
| 3 | 72 | 89 | 4.0 |
| 4 | 72 | 89 | 3.0 |
| 5 | 72 | 89 | 2.4 |
| 6 | 72 | 89 | 2.4 |
| 7 | 72 | 89 | 2.4 |
| 8 | 72 | 89 | 2.4 |
| 9 | 72 | 89 | 2.4 |
| 10 | 77 | 89 | 1.6 |
| 11 | 72 | 89 | 1.6 |
| 12 | 72 | 89 | 1.6 |
| 13 | 72 | 89 | 1.6 |
| 14 | 72 | 88 | 1.6 |
| 15 | 72 | 88 | 1.6 |
| 16 | 72 | 88 | 1.6 |
| 17 | 72 | 88 | 1.6 |
| 18 | 72 | 92 | 1.6 |
| 19 | 72 | 99 | 1.6 |
| 20 | 68 | 112 | 1.6 |
| 21 | 60 | 135 | 1.6 |

Bulked fractions 9-18 have a herbaceous, fruity, cedarleaf-like, rosy, tobacco-like aroma with rosy, minty and dried-fruit undertones.

The compound having the structure:

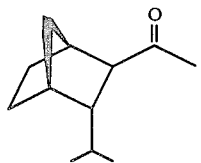

is three times as intense and more aesthetically pleasing than the compound having the structure:

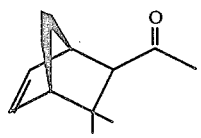

prepared according to U.S. Pat. No. 3,858,358 issued on Dec. 3, 1974.

FIG. 4 is the NMR spectrum for the mixture of "exo" and "endo" isomers defined according to the structure:

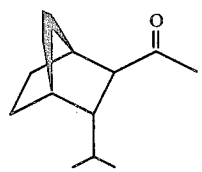

(conditions: Field strength: 100 MHz; Solvent: $CFCl_3$).

FIG. 5 is the infra-red spectrum for the mixture of isomers having the structure:

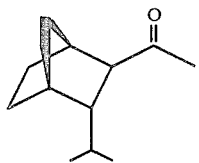

EXAMPLE II

PREPARATION OF 1-(ALPHA HYDROXY ETHYL)-2-ISOPROPYLNORBORNENE

Reaction:

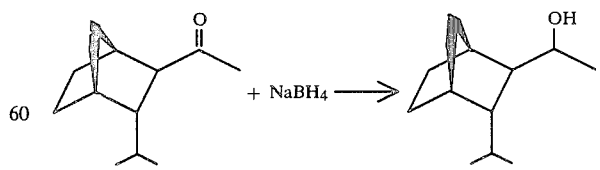

Into a 3-liter reaction vessel equipped with stirrer, thermometer, reflux condenser and heating mantle is placed a mixture of 150 grams of sodium borohydride and 2 liters of anhydrous isopropenol. The resulting mixture is heated to 70° C. and while maintained at 70°

C., over a period of one hour, the compound having the structure:

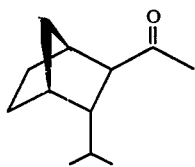

prepared according to Example I (540 grams) is added to the reaction mass.

At the end of the one hour feeding period, the reaction mass is heated to reflux and refluxed for a period of 5.5 hours.

At the end of the 5.5 hour period, the reaction mass is added to 5 liters of water. Dilute hydrochloric acid is added until the reaction mass exists in two phases. The reaction mass is then washed and neutralized with aqueous sodium carbonate. The resulting organic phase is then fractionally distilled yielding the following fractions:

| Fraction No. | Vapor Temp. (°C.) | Liquid Temp. (°C.) | Vacuum mm/Hg. Mercury |
|---|---|---|---|
| 1 | 23/30 | 23/110 | 100/3 |
| 2 | 95 | 100 | 4.0 |
| 3 | 93 | 108 | 9.1 |
| 4 | 100 | 110 | 9.1 |
| 5 | 160 | 108 | 9.1 |
| 6 | 98 | 108 | 1.1 |
| 7 | 98 | 108 | 1.1 |
| 8 | 98 | 108 | 1.1 |
| 9 | 98 | 108 | 1.1 |
| 10 | 98 | 108 | 1.1 |
| 11 | 98 | 108 | 1.1 |
| 12 | 98 | 108 | 1.1 |

Fraction 6–13 of the foregoing distillation are bulked.

These fractions have a minty, sweaty, camphoraceous, woody and earthy aroma profile with woody, minty, sweaty, camphoraceous and earthy undertones.

FIG. 6 is the GLC profile for the crude reaction product containing the compound having the structure:

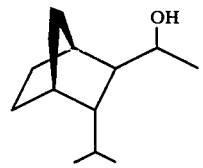

(Conditions: Carbowax column programmed at 180° C. isothermal). The peak indicated by reference numeral "60" is the peak for the mixture of "exo" and "endo" isomers of the compound having the structure:

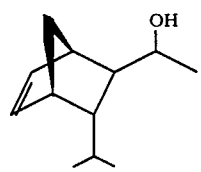

FIG. 7 is the NMR spectrum for the mixture of "exo" and "endo" isomers having the structure:

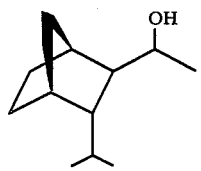

(Conditions: Field strength: 100 MHz; Solvent: $CFCl_3$).

FIG. 8 is the infra-red spectrum for the mixture of "exo" and "endo" isomers having the structure:

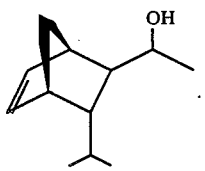

EXAMPLE III

PREPARATION OF REACTION PRODUCT OF 2-METHYL-3-HEXEN-5-ONE WITH METHYL BICYCLOPENTADIENE

Reaction:

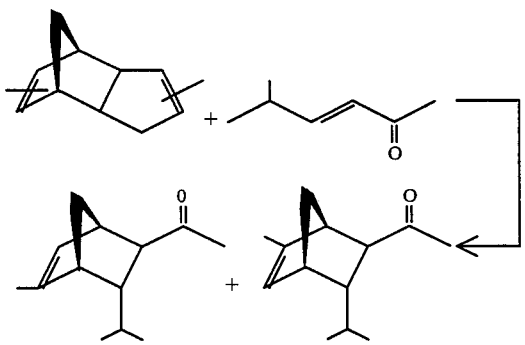

Into an autoclave is charged 480 grams (3 moles) of dimethyl dicyclopentadiene and 672 grams (6 moles) of 2-methyl-3-hexen-5-one. The autoclave is sealed and heated to 150° C. at 150 psig pressure. The autoclave is maintained at 150° C. and 150 psig pressure for a period of 1.5 hours. At the end of the 1.5 hour period, the autoclave is cooled and opened and the contents distilled. The first distillation takes place on a short-path column yielding the following fractions:

| Fraction No. | Vapor Temp. (°C.) | Liquid Temp. (°C.) | Vacuum mm/Hg. Mercury |
|---|---|---|---|
| 1 | 27/60 | 23/80 | 200/30 |
| 2 | 67 | 93 | 30.0 |
| 3 | 87 | 106 | 30.0 |
| 4 | 98 | 112 | 30.0 |
| 5 | 101 | 115 | 25.0 |
| 6 | 105 | 115 | 25.0 |
| 7 | 95 | 145 | 4.0 |
| 8 | 100 | 185 | 3.0 |

Fractions 2–8 are bulked and redistilled on a 12"×1.5" Goodloe column yielding the following fractions:

| Fraction No. | Vapor Temp. (°C.) | Liquid Temp. (°C.) | Vacuum mm/Hg. Mercury |
|---|---|---|---|
| 1 | 23/10 | 23/100 | 2/3 |
| 2 | 77 | 103 | 2.0 |
| 3 | 73 | 105 | 1.6 |
| 4 | 73 | 101 | 1.6 |
| 5 | 75 | 105 | 1.6 |
| 6 | 75 | 105 | 1.6 |
| 7 | 75 | 105 | 1.6 |
| 8 | 75 | 105 | 1.6 |
| 9 | 75 | 105 | 1.6 |
| 10 | 75 | 105 | 1.6 |
| 11 | 76 | 108 | 1.6 |
| 12 | 76 | 108 | 1.6 |
| 13 | 75 | 110 | 1.6 |
| 14 | 75 | 115 | 1.6 |
| 15 | 76 | 155 | 1.6 |

Fractions 4–12 are bulked. The bulked fractions have a herbaceous, spicy, green, rosy, fruity aroma with piney, minty, rosy, spicy, melony and fruity undertones.

FIG. 9 is the GLC profile for the crude reaction product containing mixtures of "exo" and "endo" isomers of the compounds having the structures:

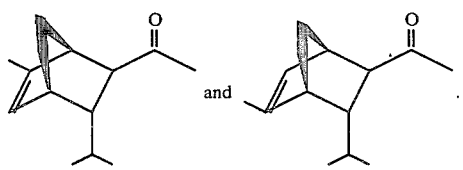

The peaks indicated by reference numerals "90" and "91" are peaks for the "exo" and "endo" isomers of the compounds having the structures:

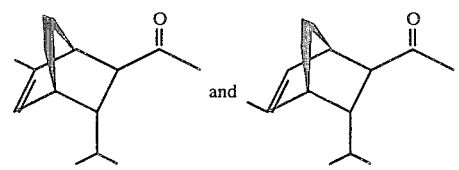

(conditions: SE-30 column programmed at 150° C. isothermal).

FIG. 10 is the NMR spectrum for the mixture of "exo" and "endo" isomers of the compounds having the structures:

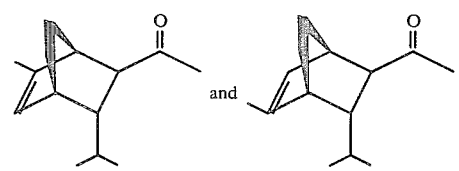

(Conditions: Field strength: 100 MHz; Solvent: CFCl₃).

FIG. 11 is the infra-red spectrum for the mixture of "exo" and "endo" isomers of the compounds having the structures:

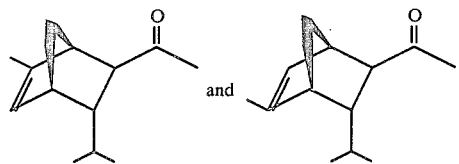

EXAMPLE IV

PREPARATION OF REACTION PRODUCT OF DIMETHYL CYCLOPENTADIENE WITH 2-METHYL-3-HEXEN-5-ONE AND HYDROGENATION THEREOF

Reactions:

A.

B.

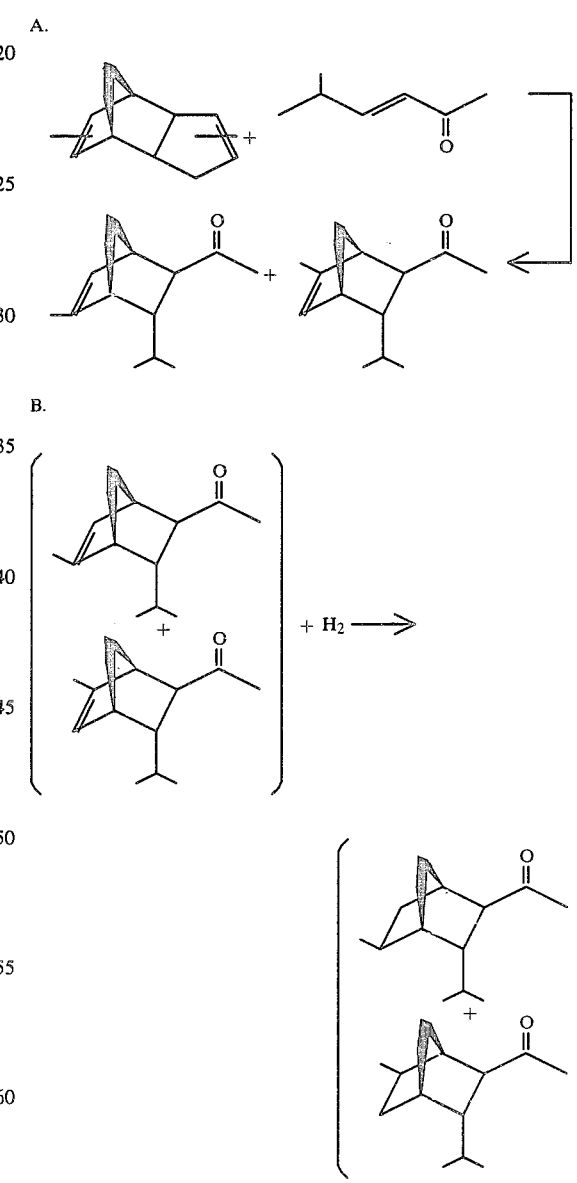

Into an autoclave is placed 480 grams (3 moles) of dimethyl dicyclopentadiene and 672 grams (6 moles) of 2-methyl-3-hexen-5-one. The autoclave is sealed and heated to 150° C. at 150 psig. The autoclave is maintained at 150° C. and 150 psig for a period of 0.5 hours. At the end of the 0.5 hour period, the autoclave is cooled and the contents are removed and placed into a 2-liter Parr shaker along with product of two other runs. Also added to the Parr shaker are 5 grams of 5% palladium on carbon hydrogenation catalyst. The Parr shaker is sealed and pressurized with hydrogen to 50 psig at a temperature of 40° C. The hydrogenation at 50 psig and 40° C. continues over a period of seven hours. At the end of the seven hour period, the Parr shaker is cooled and opened and the contents are filtered and distilled on a fractional distillation column yielding the following fractions:

| Fraction No. | Vapor Temp. (°C.) | Liquid Temp. (°C.) | Vacuum mm/Hg. Mercury |
| --- | --- | --- | --- |
| 1 | 23/82 | 23/100 | 2/3 |
| 2 | 74 | 100 | 2.0 |
| 3 | 74 | 100 | 1.6 |
| 4 | 74 | 100 | 1.6 |
| 5 | 74 | 100 | 1.6 |
| 6 | 74 | 100 | 1.6 |
| 7 | 74 | 100 | 1.6 |
| 8 | 74 | 100 | 1.6 |
| 9 | 75 | 100 | 1.6 |
| 10 | 75 | 100 | 1.6 |
| 11 | 75 | 100 | 1.6 |
| 12 | 75 | 100 | 1.6 |
| 13 | 75 | 100 | 1.6 |
| 14 | 77 | 100 | 1.6 |
| 15 | 75 | 155 | 1.6 |

Fractions 7–13 are bulked and the bulked fractions have an excellent highly intense woody and camphoraceous aroma.

FIG. 12 is the GLC profile for the crude reaction product of this example containing a mixture of "exo" and "endo" isomers of the compounds having the structures:

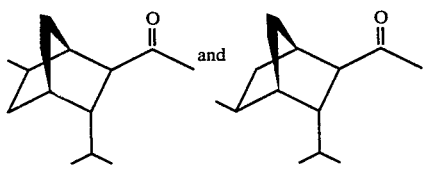

The peaks indicated by reference numerals "120" and "121" are peaks for the "exo" and "endo" isomers of the compounds having the structures:

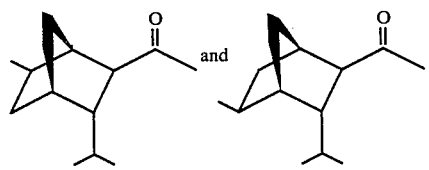

(GLC Conditions: SE-30 column programmed at 180° C. isothermal).

FIG. 13 is the NMR spectrum for the mixture of "exo" and "endo" isomers of the compounds having the structures:

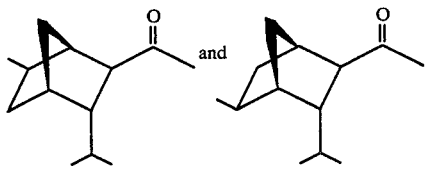

(Conditions: Field strength: 100 MHz; Solvent: CFCl₃).

FIG. 14 is the infra-red spectrum for the mixture of "exo" and "endo" isomers of the compounds having the structures:

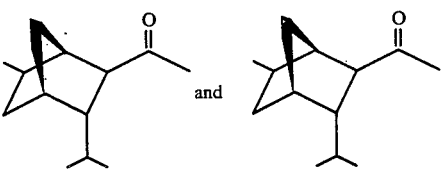

EXAMPLE V

HERBAL FRAGRANCES

The following mixtures are prepared:

| Ingredients | Parts by Weight | | | | |
| --- | --- | --- | --- | --- | --- |
| | V(A) | V(B) | V(C) | V(D) | V(E) |
| Amyl cinnamic aldehyde | 20 | 20 | 20 | 20 | 20 |
| Phenyl acetaldehyde dimethyl acetal | 4 | 4 | 4 | 4 | 4 |
| Thyme oil white | 8 | 8 | 8 | 8 | 8 |
| Sauge sclaree French | 8 | 8 | 8 | 8 | 8 |
| Galbanum oil | 4 | 4 | 4 | 4 | 4 |
| Geranyl acetate | 10 | 10 | 10 | 10 | 10 |
| Juniper berry oil | 4 | 4 | 4 | 4 | 4 |
| Methyl octynyl carbonate | 2 | 2 | 2 | 2 | 2 |
| Linalyl acetate | 10 | 10 | 10 | 10 | 10 |
| Dihydro methyl jasmonate | 20 | 20 | 20 | 20 | 20 |
| Gamma methyl gamma cyclohexyl butyrolactone | 12 | 12 | 12 | 12 | 12 |
| Limonene carboxaldehyde | 12 | 12 | 12 | 12 | 12 |
| A mixture of "exo" and "endo" isomers having the structure: 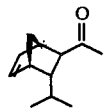 prepared according to Example I. | 3 | 0 | 0 | 0 | 0 |
| A mixture of "exo" and "endo" isomers of the compound having the structure: 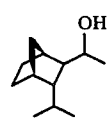 | 0 | 3 | 0 | 0 | 0 |
| A mixture of "exo" and "endo" isomers of the compound having the structure: 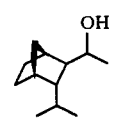 | 0 | 0 | 3 | 0 | 0 |

-continued

| Ingredients | Parts by Weight | | | | |
|---|---|---|---|---|---|
| | V(A) | V(B) | V(C) | V(D) | V(E) | prepared according to
Example II.
A mixture of "exo" and
"endo" isomers of the
compounds having
the structures:

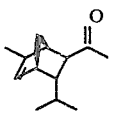

and

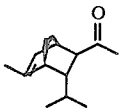

prepared according
to Example III.
A mixture of "exo" and    0   0   0   0   3
"endo" isomers of the
compounds having
the structures:

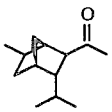

and

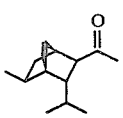

prepared according to
Example IV.

0   0   0   3   0

The perfume composition of Example V(A), as a result of the 1-oxoalkyl-2-isopropylnorbornane derivatives added to it has a strong herbaceous aroma with sweet, minty, fruity, green and cucumber topnotes.

The perfume composition of Example V(B), as a result of the 1-oxoalkyl-2-isopropylnorbornane derivatives added to it has an intense herbaceous aroma with fruity, rosy, cedarleaf-like and tobacco-like topnotes and rosy, minty, herbaceous and dried-fruit undertones.

The perfume composition of Example V(C) has a herbaceous aroma with aesthetically pleasing, minty, faint, sweaty, woody, camphoraceous and earthy topnotes and woody, minty, aesthetically pleasing, sweaty, camphoraceous and earthy undertones.

The perfume composition of Example V(D), as a result of the 1-oxoalkyl-2-isopropylnorbornane derivatives being added to it has an excellent strong herbaceous aroma with spicy, green, rosy and fruity topnotes and piney, minty, rosy, spicy, melony and fruity undertones.

The perfume composition of Example V(E) has an excellent herbaceous aroma with strong woody topnotes and woody undertones.

EXAMPLE VI

PREPARATION OF A COSMETIC POWDER COMPOSITION

A cosmetic powder is prepared by mixing in a ball mill 100 grams of talcum powder with 0.25 grams of the perfume substance set forth in Table I below. The resulting cosmetic powders have excellent aroma profiles as indicated in Table I below:

TABLE I

| Perfume Substance | Aroma Profile Imparted |
|---|---|
| Mixture of "exo" and "endo" isomers produced according to Example I having the structure:  prepared according to Example I. | A sweet, herbaceous, minty, fruity and green cucumber-like aroma profile. |
| Mixture of "exo" and "endo" isomers having the structure:  | A strong herbaceous, fruity, rosy, cedarleaf-like and tobacco-like aroma with rosy, minty, herbaceous and dried-fruit undertones. |
| Mixture of "exo" and "endo" isomers produced according to Example II having the structure:  | A minty, sweaty, woody, camphoraceous and earthy aroma profile with woody, minty, sweaty, camphoraceous and earthy undertones. |
| Mixture of "exo" and "endo" isomers of the compounds having the structures:  and  prepared according to Example III. | A strong herbaceous, spicy, green, rosy and fruity aroma profile with piney, minty, rosy, spicy, melony and fruity undertones. |
| Mixture of "exo" and "endo" isomers having the structures:  and  prepared according to Example IV. | A woody and camphoraceous aroma profile. |
| Perfume composition of Example V(A). | A strong herbaceous aroma with sweet, minty, fruity, green and cucumber topnotes. |
| Perfume composition of Example V(B). | An intense herbaceous aroma with fruity, rosy, cedarleaf-like and |

TABLE I-continued

| Perfume Substance | Aroma Profile Imparted |
|---|---|
| | tobacco-like topnotes and rosy, minty, herbaceous and dried-fruit undertones. |
| Perfume composition of Example V(C). | A herbaceous aroma with aesthetically pleasing, minty, faint, sweaty, woody, camphoraceous and earthy topnotes and woody, minty, aesthetically pleasing, sweaty, camphoraceous and earthy undertones. |
| Perfume composition of Example V(D). | An excellent strong herbaceous aroma with spicy, green, rosy and fruity topnotes and piney, minty, rosy, spicy, melony and fruity undertones. |
| Perfume composition of Example V(E). | An excellent herbaceous aroma with strong woody topnotes and woody undertones. |

EXAMPLE VII

PREPARATION OF SOAP COMPOSITION

100 Grams of soap chips are mixed with 1 gram of each of the perfume materials of Table I of Example VI until a substantially homogeneous composition is obtained. The resulting mixture is melted and maintained at 10 atmospheres pressure at a temperature of 180° C. for a period of 4 hours. At the end of the 4 hour period, the resulting homogeneous mixture is cooled. The perfumed soap composition manifests an excellent aroma character as set forth in Table I of Example VI.

EXAMPLE VIII

PREPARATION OF A DETERGENT COMPOSITION

A granular detergent composition is prepared according to Example IX of Canadian Pat. No. 1,004,566 (the disclosure of which is incorporated by reference herein) containing the following ingredients:

| Component | Weight % |
|---|---|
| Anhydrous sodium carbonate | 30.0 |
| Hydrated sodium silicate (81.5% solids, $SiO_2:Na_2O$ ratio-2.1:1 by weight) | 20.0 |
| Coconut alcohol condensed with 6 molar proportions of ethylene oxide | 10.0 |
| Sodium citrate dihydrate | 10.0 |
| Sodium dichlorocyanurate dihydrate | 3.8 |
| Polyethylene glycol (available under the trademark Carbowax 4000 M.W. 3000-3700) | 2.0 |
| Dimethyl silicone | 0.8 |
| Anhydrous sodium sulfate | 15.5 |
| Perfume substance as set forth in Table I of Example VI | 5.9 |

The resulting detergent compositions have excellent aromas as set forth in Table I of Example VI.

EXAMPLE IX

PREPARATION OF A DETERGENT COMPOSITION

A detergent is prepared from the following ingredients according to Example I of Canadian Pat. No. 1,007,948 (the disclosure of which is incorporated herein by reference):

| Ingredients | Parts by Weight |
|---|---|
| Neodol 45-11 (a $C_{14}$-$C_{15}$ alcohol ethoxylated with 11 moles of ethylene oxide) | 12 |
| Sodium carbonate | 55 |
| Sodium citrate | 20 |
| Sodium sulfate, water brighteners | q.s. |

The detergent is a phosphate-free detergent. A total of 100 grams of this detergent is admixed individually with 0.15 grams of each of the perfumery substances of Table I of Example VI. Each of the detergents has excellent aromas as set forth in Table I of Example VI.

EXAMPLE X

PERFUMED LIQUID DETERGENT

Concentrated liquid detergents with aroma nuances as set forth in Table I of Example VI containing 0.10%, 0.15% and 0.20% of each of the perfumery substances of Table I of Example VI are prepared. They are prepared by adding and homogeneously admixing the appropriate quantity of each of the perfumery substances of Table I of Example VI in the liquid detergent. The detergents all possess excellent aromas as set forth in Table I of Example VI.

EXAMPLE XI

COLOGNE AND HANDKERCHIEF PERFUMES

The perfume substances of Table I of Example VI are each incorporated separately into colognes at concentrations of 1.5%, 2.0%, 2.5%, 3.0%, 4.0% and 5.0% in 70%, 75%, 80%, 85% and 90% aqueous ethanol solutions; and into handkerchief perfumes at concentrations of 15%, 20%, 30% and 40% (in 80%, 85%, 90% and 95% aqueous ethanol solutions). Distinct and definitive strong fragrances are imparted to the colognes and to the handkerchief perfumes at the levels indicated according to the aroma profiles as set forth in Table I of Example VI.

EXAMPLE XII

PERFUMED PLASTICS

Scented polyethylene pellets having pronounced aromas as set forth in Table I of Example VI are prepared as follows:

Seventy-five pounds of polyethylene having a melting point of about 220° F. is heated to about 230° F. in a container of the kind illustrated in FIGS. 15 and 16. Twenty-five pounds of the fragrance materials of Table I of Example VI is then quickly added, separately, to the liquified polyethylene, the lid 228 is put in place and the agitating means 273 are actuated. The temperature is maintained at about 225° F. and the mixing is continued for about 15 minutes. The valve "V" is then opened to allow flow of the molten polyethylene enriched with the aroma containing material of one of the fragrance materials of Table I of Example VI to exit through the orifices 234. The liquid falling through the orifices 234 solidifies almost instantaneously upon impact with the moving cooled conveyor 238. Polyethylene beads or pellets 224 having pronounced aromas as set forth in Table I of Example VI are thus formed. Analysis demonstrates that the pellets contain about 25% of the aroma substance (separately) of Table I of Example VI so that almost no loss in the scenting substance occur. These pellets may be called "master pellets".

Fifty pounds of the aroma substance-containing master pellets are then added to one thousand pounds of unscented polyethylene powder and the mass is heated to the liquid state. The liquid is molded into thin sheets of films. The thin sheets of films have pronounced aromas as set forth in Table I of Example VI. The sheets of films are cut into strips ¼" in width×3" in length and employed in standard air freshening apparatus.

On operation of the standard air freshening apparatus as a room air freshener, after four minutes, the room has an aesthetically pleasing aroma as set forth in Table I of Example VI (on an example-by-example basis) with no foul odor being present.

EXAMPLE XIII

One hundred pounds of polypropylene are heated to about 300° F. Thirty pounds of the essence of the perfume substances as described in Table I of Example VI, supra, are added to the liquified polypropylene. The procedure is carried out in the apparatus shown in FIGS. 15 and 16. After mixing for about eight minutes, the valve "V" is opened to allow the exit of polypropylene scented material mixture whereby solid pellets having a pronounced perfume smell are formed on the conveyor. The pellets thus obtained are then admixed with about twenty times their weight of unscented polypropylene and the mixture is heated and molded into "spaghetti" tows. The spaghetti tows are cut into small cylinders approximately 0.1 inches in length×0.02 inches in diameter. The cylinders have a strong and pleasant perfumed smell and scent as set forth in Table I of Example VI, supra.

The cylinders are used in standard air freshening apparatus to produce aesthetically pleasing faint scent with no foul odor in environments surrounding the air freshening apparatus the scents described in Table I of Example VI, supra.

What is claimed is:

1. A process for augmenting or enhancing the aroma of a consumable material selected from the group consisting of perfume compositions, colognes and perfumed articles comprising the step of adding to said consumable material, an aroma augmenting or enhancing quantity of at least one 1-oxoalkyl-2-isopropylnorbornane derivative defined according to the structure:

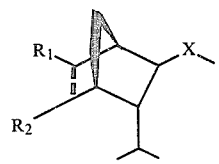

wherein X represents a moiety selected from the group consisting of:

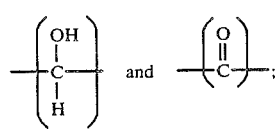

wherein the dashed line represents a carbon-carbon double bond or a carbon-carbon single bond and wherein $R_1$ and $R_2$ represent hydrogen or methyl with the proviso that $R_1$ and $R_2$ are not both methyl.

2. The process of claim 1 wherein the 1-oxoalkyl-2-isopropylnorbornane derivative has the structure:

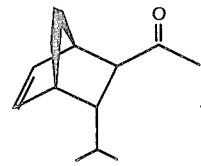

3. The process of claim 1 wherein the 1-oxoalkyl-2-isopropylnorbornane has the structure:

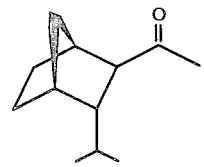

4. The process of claim 1 wherein the 1-oxoalkyl-2-isopropylnorbornane derivative has the structure:

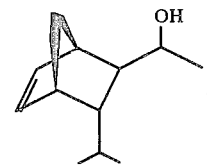

5. The process of claim 1 wherein the 1-oxoalkyl-2-isopropylnorbornane derivative are a mixture of "exo" and "endo" isomers having the structures:

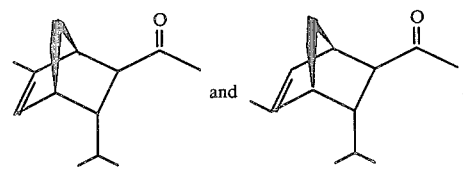

6. The process of claim 1 wherein the 1-oxoalkyl-2-isopropylnorbornane derivatives are a mixture of "endo" and "exo" isomers having the structures:

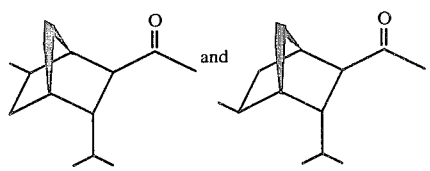

7. An 1-oxoalkyl-2-isopropylnorbornane derivative defined according to the structure:

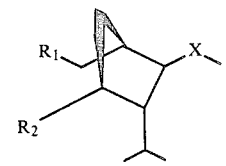

wherein the dashed line represents a carbon-carbon double bond or a carbon-carbon single bond; wherein X represents a moiety having a structure selected from the group consisting of:

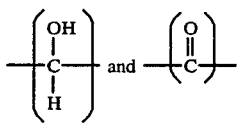

and wherein R₁ and R₂ each represent hydrogen or methyl with the provisos:

(a) that $R_1$ and $R_2$ are not both methyl;

(b) that $R_1$ and $R_2$ are not both hydrogen when the dashed line is a double bond and X is the moiety:

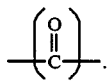

8. The 1-oxoalkyl-2-isopropylnorbornane derivative of claim 7 having the structure:

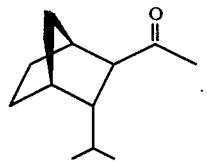

9. The 1-oxoalkyl-2-isopropylnorbornane derivative of claim 7 having the structure:

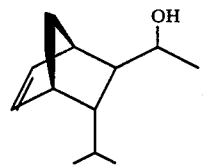

10. The 1-oxoalkyl-2-isopropylnorbornane derivative of claim 7 having the structure:

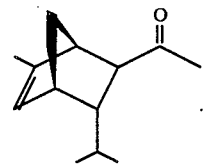

11. The 1-oxoalkyl-2-isopropylnorbornane derivative of claim 7 having the structure:

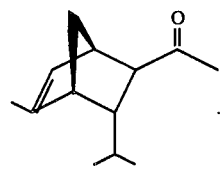

12. The 1-oxoalkyl-2-isopropylnorbornane derivative of claim 7 having the structure:

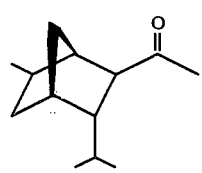

13. The 1-oxoalkyl-2-isopropylnorbornane derivative of claim 7 having the structure:

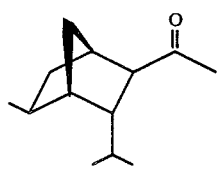

* * * * *